(12) United States Patent
Kigata et al.

(10) Patent No.: US 7,432,412 B2
(45) Date of Patent: Oct. 7, 2008

(54) ABSORBENT ARTICLE

(75) Inventors: Tetsuyuki Kigata, Tochigi (JP); Shinsuke Nagahara, Tochigi (JP)

(73) Assignee: Kao Corporation, Tokyo (JP)

( * ) Notice: Subject to any disclaimer, the term of this patent is extended or adjusted under 35 U.S.C. 154(b) by 61 days.

(21) Appl. No.: 11/284,901

(22) Filed: Nov. 23, 2005

(65) Prior Publication Data
US 2006/0142710 A1 Jun. 29, 2006

(30) Foreign Application Priority Data
Dec. 28, 2004 (JP) ............... 2004-379412
Dec. 28, 2004 (JP) ............... 2004-379413

(51) Int. Cl.
*A61F 13/15* (2006.01)
(52) U.S. Cl. ............ 604/367; 604/361; 604/366; 604/385.01; 604/365; 604/362; 604/364
(58) Field of Classification Search ........... 604/361, 604/367, 385.28, 366, 365, 385.01, 362, 604/381, 364; 116/200, 206, 202
See application file for complete search history.

(56) References Cited

U.S. PATENT DOCUMENTS
2004/0015145 A1 * 1/2004 Miura et al. .......... 604/367

FOREIGN PATENT DOCUMENTS
JP 3021237 U 11/1995
JP 2002-360620 A 12/2002
WO WO-2004/006818 A1 1/2004

* cited by examiner

*Primary Examiner*—Jacqueline F. Stephens
(74) *Attorney, Agent, or Firm*—Birch, Stewart, Kolasch & Birch, LLP

(57) ABSTRACT

An absorbent article having a substantially oblong rectangular absorbent body A composed of a topsheet 2, a backsheet 3, and an absorbent core 4 between the topsheet 2 and the backsheet 3. The absorbent article further has a pair of side sheets 5 as leak preventive side members on its skin facing side C of the absorbent body A. The leak preventive side members have a pattern P printed with ink in a configuration such that the printed ink is substantially kept away from contact with the skin of a wearer.

13 Claims, 20 Drawing Sheets

ABSORBENT ARTICLE

TECHNICAL FIELD

The present invention relates to absorbent articles including sanitary napkins, panty liners, and incontinence pads.

BACKGROUND ART

JP-A-2002-360620 discloses an absorbent article having a pattern indicative of attachment direction printed on the widthwise middle thereof to inform a user of the attachment direction.

WO 2004/006818 discloses an absorbent article in which the backsheet has a pattern printed on its wearer facing side in a region outside of the absorbent core. The printed pattern is seen from the skin facing side through the topsheet so as to help reduce wearer's depressed feeling.

Japanese registered utility model 3021237 discloses an absorbent article in which the skin facing side of a whole region outside of the absorbent core is colored solid so as to make the absorbent article less outstanding even when a wearer wears a deeply colored undergarment.

DISCLOSURE OF THE INVENTION

Problems to be Solved:

An absorbent article must have fundamental functions such as absorptivity and leak prevention. Any of the publications cited above gives no consideration to connection of patterning or coloring to the fundamental functions.

While improving leak prevention of an absorbent article has been an issue of concern, any of the publications is absent on taking advantage of pattern printing to improve leak prevention.

A first object of the present invention is to provide an absorbent article having a pattern printed on its leak preventive side members thereby to open the user's eyes to the existence of the leak preventive side members and give the user a sense of security against leakage.

A second object of the present invention is to provide an absorbent article having a pattern printed to improve leak prevention and also to make the user realize improved leak prevention and feel secured.

Means for Solving the Problems:

In a first aspect of the present invention, the first object is accomplished by an absorbent article having a substantially oblong rectangular absorbent body having a topsheet, a backsheet, and an absorbent core interposed between the topsheet and the backsheet. The absorbent article further has a pair of leak preventive side members on the skin facing side of the absorbent body. The leak preventive side members have a pattern printed in a configuration such that the printed ink is substantially kept away from contact with the skin of a wearer.

In a second aspect of the present invention, the second object is accomplished by an absorbent article having a substantially oblong rectangular absorbent body having a topsheet, a backsheet, and an absorbent core interposed between the topsheet and the backsheet. The absorbent body has a plurality of depressions in the thickness direction on the skin facing side thereof in a region outside of the absorbent core and has ink transferred to the bottom of the depressions to have a pattern printed.

PREFERRED EMBODIMENTS OF THE INVENTION

The first aspect of the present invention will be described with reference to sanitary napkins as an embodiment of the absorbent article by way of the accompanying drawings.

Figure 1:
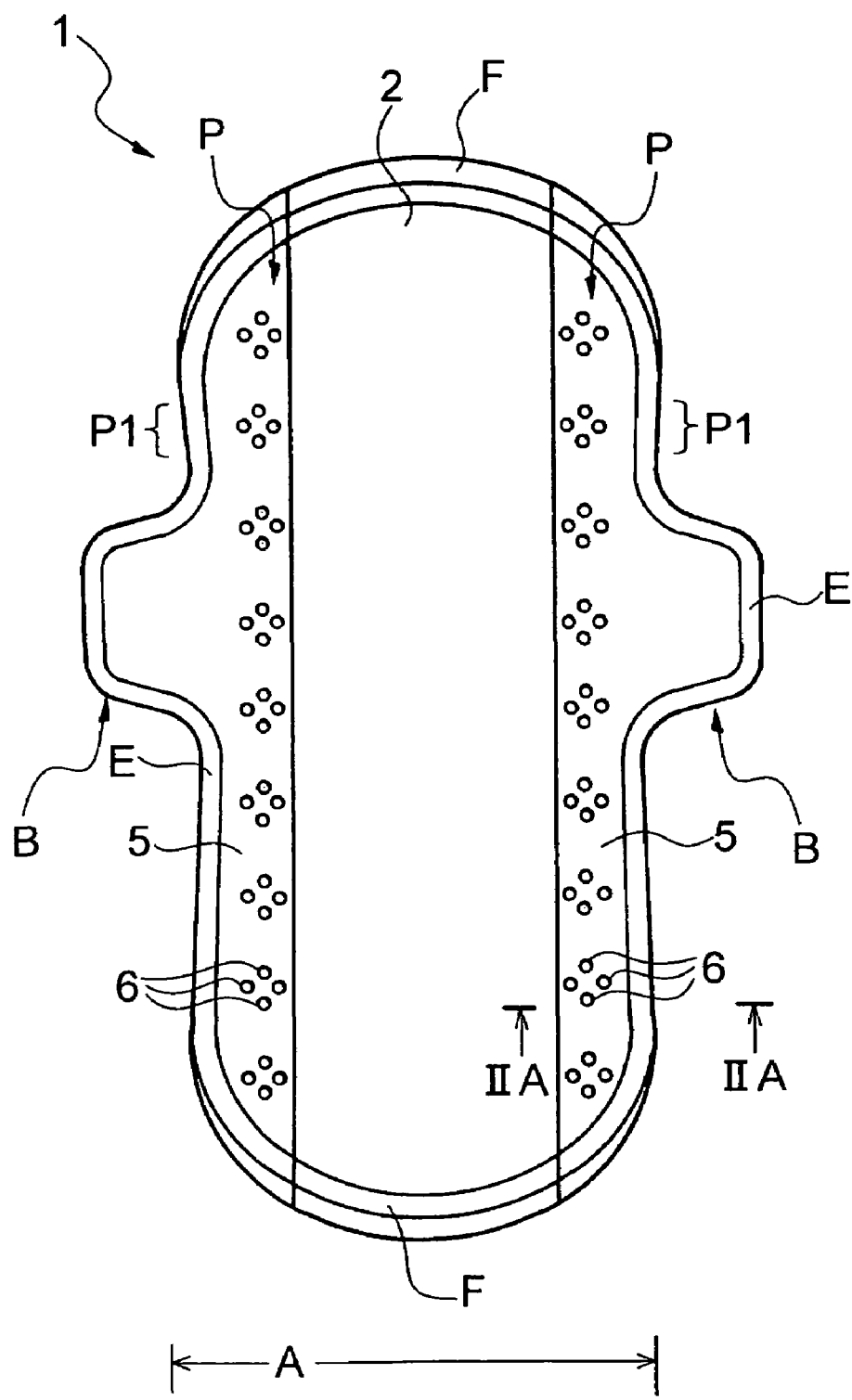
FIG. 1 is a plan view of a sanitary napkin as an embodiment of the absorbent article according to the first aspect of the invention (a first embodiment).
Figure 2A:
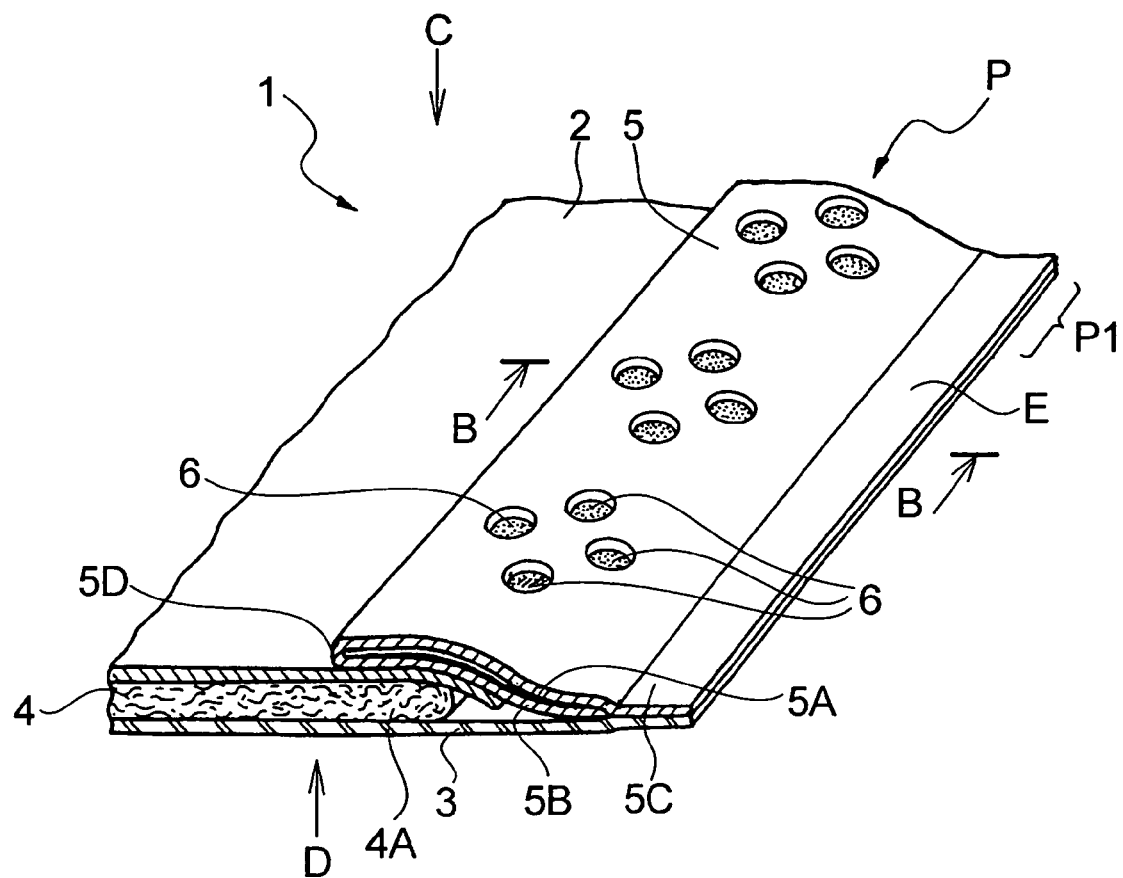
FIG. 2(a) is a fragmentary perspective view of a cross-section taken along line IIA-IIA in FIG. 1.
Figure 2B:
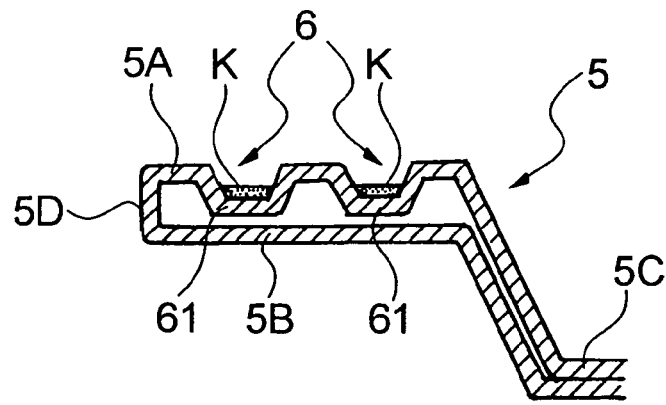
FIG. 2(b) is a schematic cross-sectional view taken along line B-B in FIG. 2(a) with the side sheet and the depressions exaggerated.

FIGS. 1, 2(a), and 2(b) illustrate a first embodiment of the sanitary napkin according to the first aspect of the invention. The sanitary napkin 1 shown in FIGS. 1, 2(a), and 2(b) has a substantially oblong rectangular absorbent body A and a pair of wings B extending laterally outward from both longitudinal sides of the absorbent body A. The absorbent body A is composed of a liquid permeable topsheet 2, a liquid impermeable backsheet 3, and a liquid retentive absorbent core 4 interposed between the topsheet 2 and the backsheet 3. The absorbent body A has a skin facing side C and a garment facing side D.

The absorbent body A has a pair of leak preventive side members (side sheets 5 described later) provided on the skin facing side C. Each leak preventive side member has a pattern P printed with ink in a configuration such that the printed ink is substantially kept away from contact with a wearer's body.

The topsheet 2 covers the entire upper side of the absorbent core 4 and slightly extends laterally outward from the longitudinally extending side portions 4A of the absorbent core 4 but is not joined with the backsheet 3. The topsheet 2 also extends outward from the front and the rear ends of the absorbent core 4 and overlaps with the backsheet in the extensions.

The topsheet 2 can be of any materials. In case where a pattern is printed on the topsheet as hereinafter described, the topsheet material should be selected from those capable of being printed. In the first embodiment, hydrophilic nonwoven fabric is used as the topsheet 2.

The backsheet 3 covers the entire lower side of the absorbent core 4 and extends laterally outward from the side portions 4A of the absorbent core 4 and longitudinally outward from the front and the rear ends of the absorbent core 4.

The backsheet 3 can be of any material. In case where a pattern is also printed on the backsheet as described later, the backsheet material should be selected from those capable of being printed. In the first embodiment, a leakproof film is used as the backsheet 3.

The absorbent core 4 can be of any material known in the art.

As illustrated in FIGS. 1 and 2(a), a pair of side sheets 5 (as leak preventive side members) are provided on the skin facing side C of the absorbent body A to cover both side portions 4A of the absorbent core 4 when seen from above over substantially the whole length of the absorbent body A. In the present embodiment, the leak preventive side members are not superposed directly on the absorbent core 4 but on the skin facing side C of the absorbent body A in a region where the absorbent core 4 exists in the thickness direction. Each side sheet 5 is placed on the skin facing side C of the absorbent body A to cover each side portion 4A of the absorbent core 4 in the plan view and extend laterally outward to cover the topsheet 2 and the backsheet 3.

The side sheet 5 can be of any materials as long as a pattern P can be formed by printing thereon such that the printed ink may not brought into direct contact with the wearer's skin. Such materials include nonwoven fabric and a plastic film. To ensure leakage prevention, liquid impermeable or hardly liquid permeable, hydrophobic nonwoven fabric or a leakproof plastic film is preferably used. In the present embodiment, a hydrophobic nonwoven fabric is used. Each side sheet 5 may be formed of either a single sheet or, in order to enhance leak prevention, cushioning effect or visibility of the pattern, a combination of two or more sheets.

As shown in FIG. 1, a pair of wings B are provided on both sides of the target zone of the absorbent body A. The wings B are formed of the lateral extension of the backsheet 3 and a laterally outer region 5C of the side sheets 5.

The backsheet 3 and the side sheets 5 are bonded together along the side edges of the absorbent body A and along the periphery of the wings B to form side seals E as shown in FIGS. 1 and 2(a). The topsheet 2 and the backsheet 3 are bonded together along the front and the rear edges of the absorbent body A to form end seals F as shown in FIG. 1.

As shown in FIG. 2(a), the backsheet 3 and the side sheets 5 are also bonded together via an adhesive (not shown) in the vicinities of the both sides of the absorbent body A and in the wings B. Each of the side sheets S extends laterally inward to cover up to the side portion 4A of the absorbent core 4 and is folded back onto the topsheet 2 to make an upper panel 5A and a lower panel 5B connected along an inner folded edge 5D. The loose edge of the lower panel 5B comes into contact with the backsheet 3. An adhesive is applied for bonding between the upper panel 5A and the lower panel 5B, between the side sheets 5 and the backsheet 3, and between the side sheets 5 and the topsheet 2.

The means for bonding in the side seals E and the end seals F and between the backsheet 3, the side sheet 5, and the topsheet 2 is not limited to an adhesive and may be heat sealing, ultrasonic sealing and the like.

The sanitary napkin 1 of the present embodiment is worn by attaching the napkin 1 to an undergarment via a hot-melt pressure-sensitive adhesive (not shown) applied to the garment facing side D of the absorbent body A and the wings B and folding the wings B over the sides of the undergarment in the crotch region to secure the napkin 1.

As illustrated in FIGS. 1, 2(a), and 2(b), the side sheet 5 has partly depressed in its thickness direction to form depressions 6 and has ink K transferred to the bottom 61 of the depressions 6 to form a printed pattern P. As illustrated in FIG. 2(b), the depressions 6 are formed by embossing the upper panel 5A of the side sheet 5. The individual depressions 6 are circles in the plan view. The individual depressions 6 preferably have a diameter or a width of 0.5 to 5.0 mm.

As illustrated in FIGS. 1 and 2(a), the pattern P is composed of pattern units P1 spacedly aligned in the longitudinal direction of the side sheet 5. Each pattern unit P1 is composed of four depressions 6 as subunits arranged at four corners of a square.

While, in FIG. 1, adjacent pattern units P1 are depicted spaced from each other by a distance larger than the length (the size in the longitudinal direction of the side sheet) of the individual units P1, adjacent pattern units P1 may be spaced at a distance smaller than the length of a single unit P1.

The ink that can be used in the present invention includes inorganic pigments and organic pigments. Organic pigments, particularly those having relatively high heat stability are preferred from the standpoint of ease of handling and smooth prosecution of steps involved, particularly in view of stability with time and the fact that the depressions 6 are preferably formed by heat embossing. Use of an adhesive, particularly a hot-melt adhesive, having the pigment incorporated therein as ink is advantageous in that the depressions 6 are formed more easily and that bonding to other members is achieved more easily. Where the side sheet 5, etc. is embossed to make depressions 6, and ink is transferred to the bottom 61 of the depressions 6 to form the pattern P as described infra, printing techniques useful to achieve such a printing method include relief printing and gravure printing.

A side sheet having a pattern P formed by transferring ink K to the bottom 61 of depressions 6, such as the side sheet 5 of the first embodiment, is obtained by various methods. The method depicted in FIG. 3 is one of them.

Figure 3:
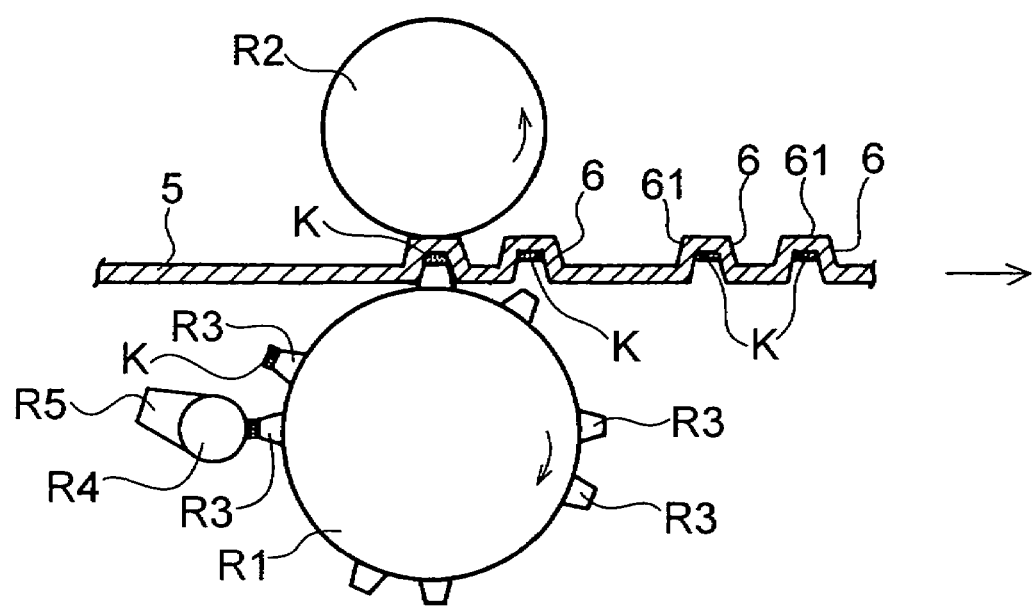
FIG. 3 schematically illustrates a method of printing a pattern on the side sheet in the first embodiment.

The method of FIG. 3 is effected using an embossing roll R1 and a backup roll R2. The embossing roll R1 has projections R3 corresponding to the depressions 6 on its peripheral surface, and the backup roll R2 has a smooth peripheral surface. In the method shown in FIG. 3, the embossing roll R1 and the backup roll R2 are located below and above a web of the side sheet 5, respectively, and an ink trough R5 containing ink K and an ink roller R4 are placed beside the embossing roll R1.

As the embossing roll R1 rotates, the ink K in the ink trough R5 adheres via the ink roller R4 to the top of the projections R3 of the embossing roll R1 as in relief printing. At the upper part of the embossing roll R1, the web of the side sheet 5 is embossed between the backup roll R2 and the projections R3 with the ink K adhered thereto. As a result, the web of the side sheet 5 has upward depressions 6 with the ink K adhered to their bottom 61.

The web of the side sheet 5 having the depressions 6 is then folded to form the side sheet 5.

Figure 4A:
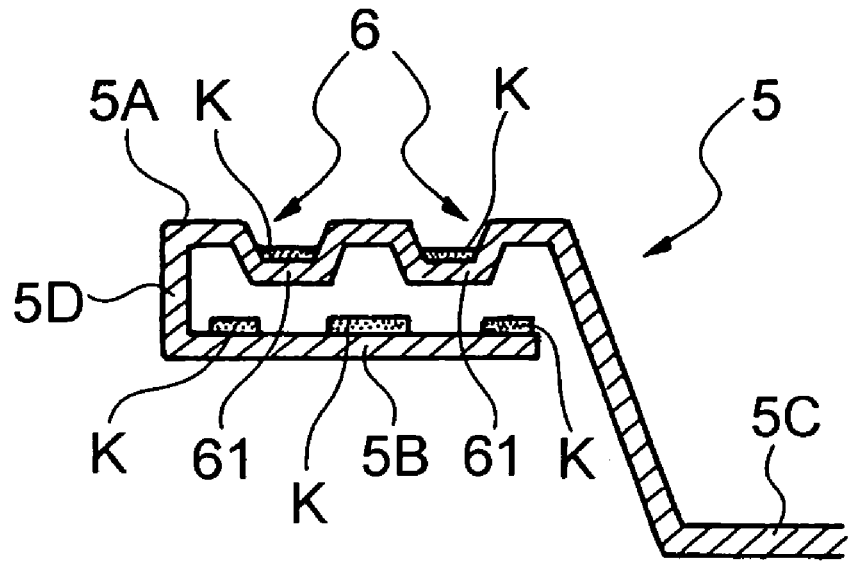
FIG. 4(a) and FIG. 4(b) are each a schematic cross-sectional view of another pattern-printed side sheet (corresponding to FIG. 2(b)).
Figure 4B:
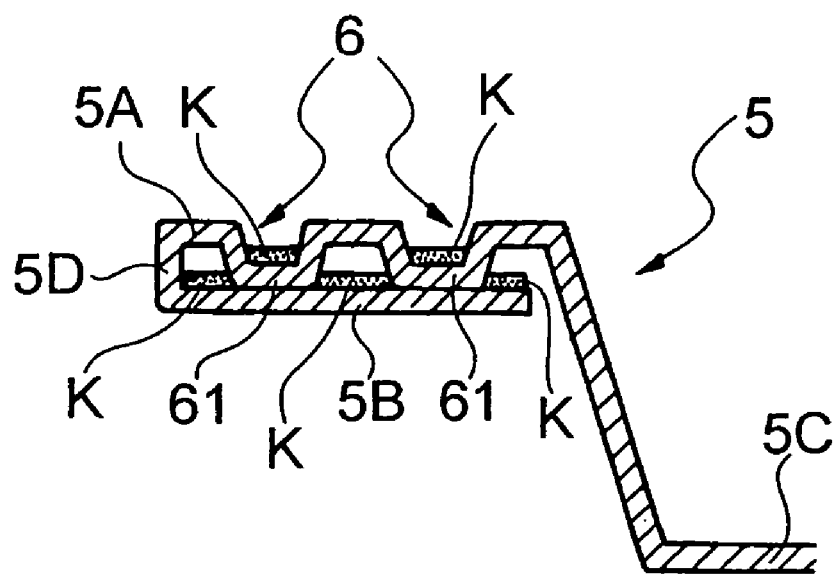

The side sheet 5 having the thus printed pattern P formed by transferring ink K to the bottom 61 of depressions 6 may have the configuration shown in FIG. 4(a) or 4(b).

The side sheet 5 shown in FIG. 4(a) has depressions 6 in its upper panel 5A with ink K adhered to the bottom 61 of the depressions 6. The lower panel 5B is not bonded to the upper panel 5A. The lower panel 5B is printed with ink K on its side facing the upper panel 5A in a region surrounding the bottom 61 of the depressions 6 of the upper panel 5A but not in a region corresponding to the bottom 61.

The side sheet 5 shown in FIG. 4(b) is the same as that in FIG. 4(a), except that the lower panel 5B is bonded to the bottom 61 of the depressions 6 formed in the upper panel 5A.

Figure 5:
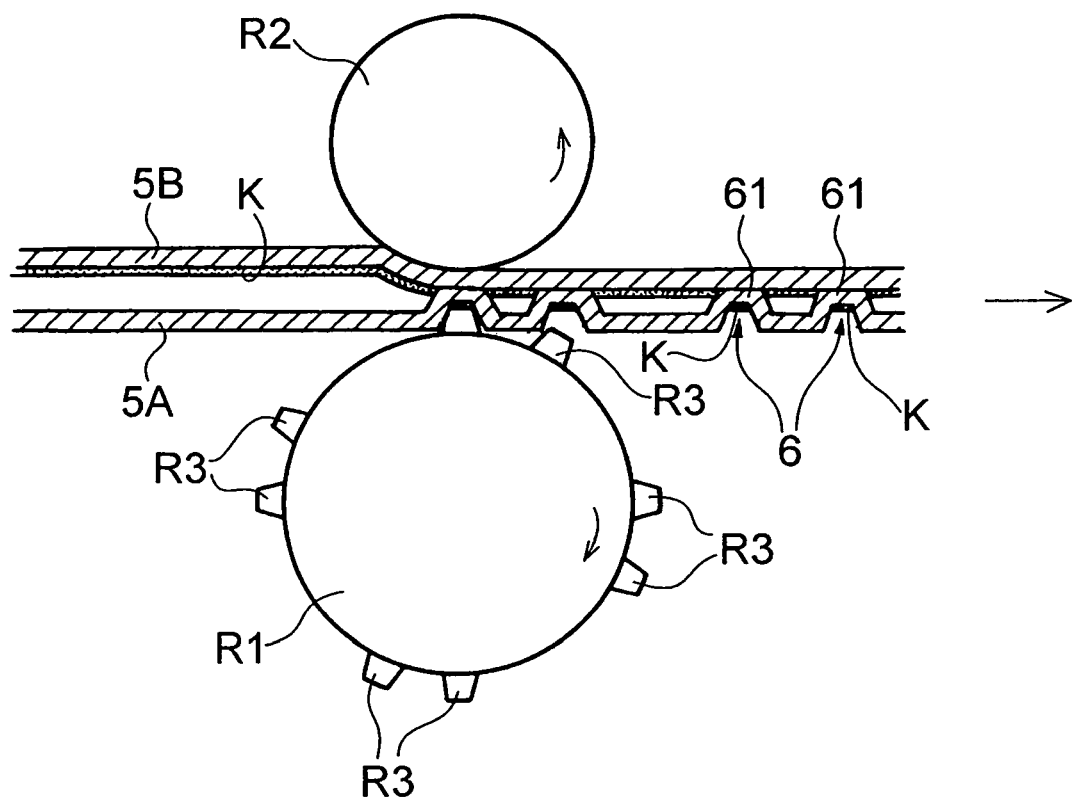
FIG. 5 schematically illustrates a method of printing a pattern on the side sheet shown in FIG. 4(a) or 4(b).

The side sheet 5 of FIG. 4(a) or 4(b) can be obtained by, for example, the method illustrated in FIG. 5. The method uses a set of an embossing roll R1 and a backup roll R2 similarly to the method shown in FIG. 3 but differs in the way of transferring ink K to the bottom 61 of the depressions 6 as follows.

To explain in more detail, ink K is applied to a predetermined width of a running web for the side sheet 5, the width being to be folded back to becomes the lower panel 5B facing the upper panel 5A. Then, the ink-applied width of the web is folded back to form the upper panel 5A and the lower panel 5B. The folded web, i.e., the upper panel 5A and the lower panel 5B are embossed between the embossing roll R1 on the side of the upper panel 5A and the backup roll R2 on the side of the lower panel 5B. As a result, depressions 6 corresponding to the projections R3 of the embossing roll R1 are formed in the upper panel 5A, and the ink K applied to the lower panel 5B penetrates into the bottom 61 of the depressions 6. In other words, the ink K is transferred to the bottom 61 of the depressions 6.

Penetrability and fixability of ink K to the bottom 61 of the depressions 6 are ensured by using highly ink-penetrable material as the side sheet 5 and an ink composition containing an adhesive and a colorant (e.g., a pigment). Penetrability of ink K is also ensured by moderately heating the embossing roll R1 (heat embossing). The surface temperature of the embossing roll is preferably controlled not to denature the material of the side sheet 5.

To form a side sheet 5 of which the lower panel 5B is not joined with the upper panel 5A as in FIG. 4(a), the embossing is carried out under conditions such that depressions 6 are formed, and the ink K penetrates the bottom 61 of the depressions 6, but the lower panel 5B is not joined with the upper panel 5A.

To form a side sheet 5 of which the lower panel 5B is joined with the bottom 61 of the depressions 6 of the upper panel 5A as in FIG. 4(b), the embossing is carried out under conditions such that depressions 6 are formed, the ink K penetrates the bottom 61 of the depressions 6, and the lower panel 5B is joined with the bottom 61 of the depressions 6 of the upper panel 5A.

Since the sanitary napkin 1 of the first embodiment has the pattern P printed on the side sheets 5, it makes a user realize the protection against leakage and feel secured. To explain in more detail, the side sheets 5, which are members for preventing side leakage, have depressions 6 with ink K transferred to the bottom 61 of the depressions 6 to form the pattern P. The pattern P makes a user clearly aware of the existence of the side sheets 5 by sight and realize the enhanced leak preventing effect by the side sheets 5. This gives a wearer a sense of security against side leakage. Additionally, the design of the pattern P lends an attractive appearance to the absorbent article. When in using hydrophobic or water-repellent ink as ink K, the ink transferred to the bottom of the depressions fills the interstices between fibers of the side sheets, etc. to produce a further enhanced effect in suppressing liquid from spreading, which provides particularly high leakproofness.

Furthermore, liquid spreading in the side sheets 5 will be blocked by the pattern P, or liquid spreading on the surface (the skin facing side) of the side sheets 5 will flow into the depressions 6, which provides further enhanced protection against side leakage.

Since the pattern P is printed in such a configuration that the printed pattern (ink K) is substantially kept away from direct contact with the skin of a wearer, the printed ink gives no burden to the skin.

Since the pattern P is imparted by printing with ink, the original softness of the material per se of the side sheet 5 is less damaged than when the material is patterned by heat sealing as conventionally practiced. Therefore, the patterned side sheets feel agreeable.

Figure 6:
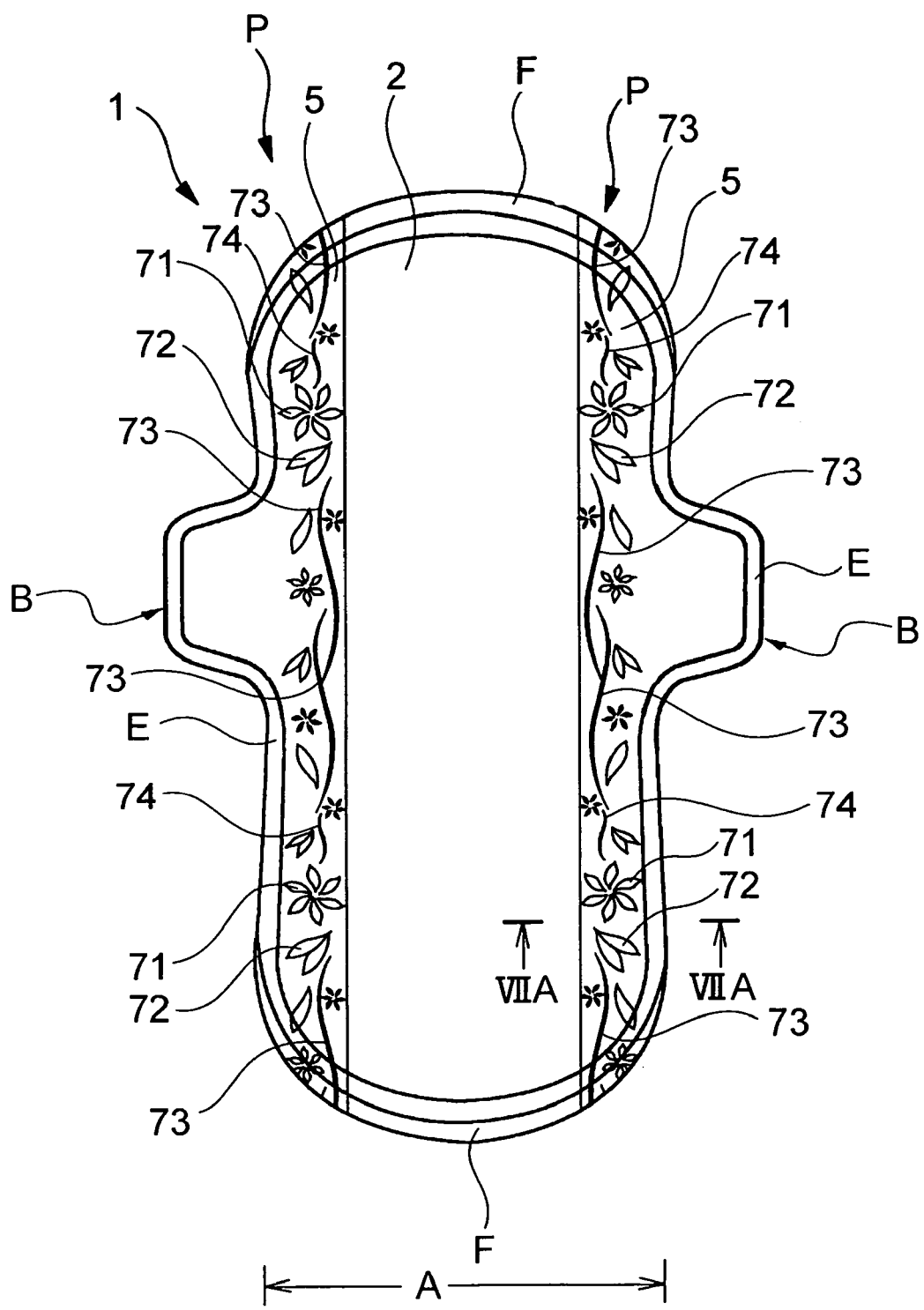
FIG. 6 is a plan view of a sanitary napkin as another embodiment of the absorbent article according to the first aspect of the invention (second embodiment).
Figure 7A:
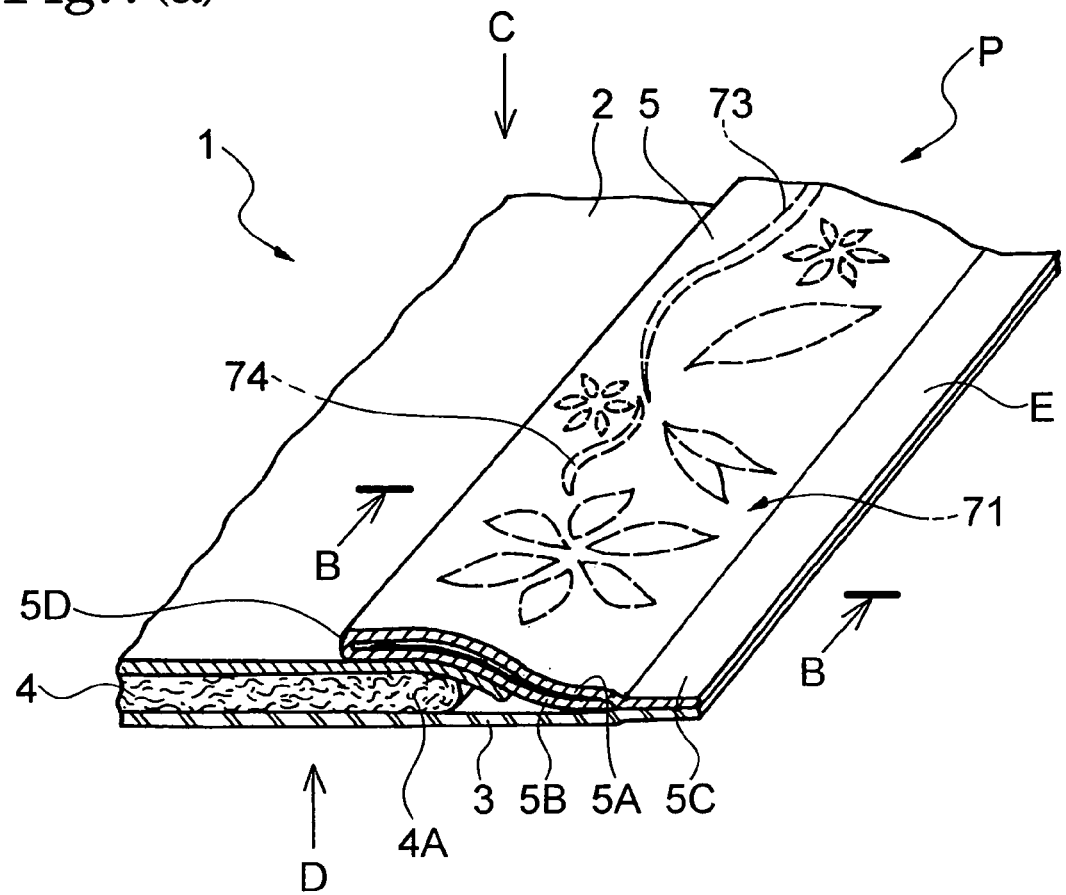
FIG. 7(a) is a fragmentary perspective view of a cross-section taken along line VIIA-VIIA in FIG. 6.
Figure 7B:
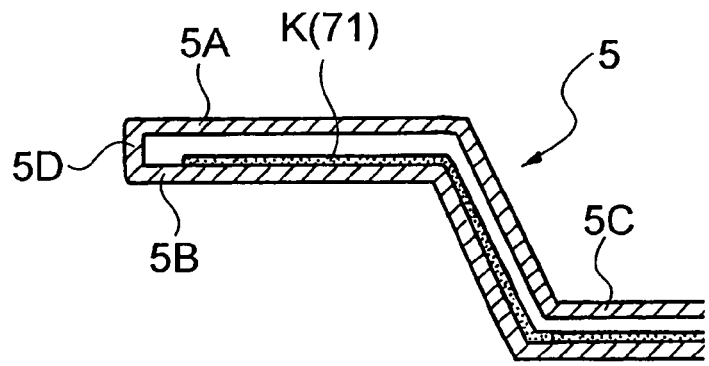
FIG. 7(b) is a schematic cross-sectional view taking along line B-B in FIG. 7(a) with the side sheet and the pattern (ink) exaggerated.

The second embodiment of the sanitary napkin according to the first aspect of the present invention will be described by referring to FIGS. 6, 7(a), and 7(b). The difference from the first embodiment resides in the construction of the patterned side sheets. The second embodiment will be described primarily with reference to the difference from the first one. In FIGS. 6, 7(a), and 7(b), elements identified with the same numerals as in the first embodiment may be identical and will not be redundantly described. Otherwise, the description relating to the first embodiment applies to the second one as appropriate.

As illustrated in FIGS. 6, 7(a), and 7(b), the sanitary napkin 1 of the second embodiment is composed mainly of an absorbent body A, a pair of wings B, and a pair of side sheets 5 similarly to the first embodiment. In the second embodiment, the pattern P is printed on the side of the side sheets 5 that does not come into direct contact with a wearer's body and is seen from the skin facing side of the napkin 1 through the side sheets 5.

In greater detail, the pattern P of the sanitary napkin 1 of the second embodiment is made up of a combination of closed loop pattern units (e.g., a petal pattern unit 71 and a leaf pattern unit 72) and wavy line pattern units (e.g., long elongated s-shape pattern unit 73 and a short elongated s-shape pattern unit 74) as depicted in FIGS. 6 and 7(a).

The pattern P is formed in each side sheet 5 over a region from right above each side portion 4A of the absorbent core 4 and extending laterally outward in the plan view. More specifically, the pattern P is formed by printing ink K on the skin facing side of the lower panel 5B of the side sheet 5 in a region from right above the side portion 4A of the absorbent core 4 and extending laterally outward from the absorbent core 4.

It is preferred that the pattern units be arranged so that the pattern P extends substantially continuously over a length of 50% or more of the whole length of the side portions 4A of the absorbent core 4. More preferably, the pattern P extends over 80% or more of the whole length of the side portions 4A to ensure leak prevention. In the second embodiment, the pattern P continuously extends over 100% of the total length of the side portions 4A of the absorbent core 4.

The expression "extend substantially continuously over N % or more of the whole length" as used herein is defined to have the following meaning. Move an imaginary straight line perpendicular to the longitudinal direction (i.e., a laterally extending straight line) in the longitudinal direction in the plan view of the absorbent article. When that line intersects the pattern P (a combination of the petal pattern units 71, the leaf pattern units 72, the long, elongated S-shaped pattern units 73, and the short, elongated S-shaped pattern units 74, etc. in the second embodiment) over a length of N % or more of the whole length, the pattern P is said to "extend substantially continuously over N % or more of the whole length".

Similarly to the first embodiment, the sanitary napkin 1 of the second embodiment having the side sheets 5 printed with the pattern P makes a user recognize the improved leak prevention thereby to give the user a sense of security.

In detail, the pattern P is formed on the side of the side sheets 5, which are provided to prevent side leakage, that does not come into direct contact with the wearer's skin and can be seen from the skin facing side through the side sheets 5. The pattern P thus makes a user clearly be aware of the existence of the leak preventive members (the side sheets 5) and realize the improved leakage preventing effect by the side sheets 5. This gives a wearer a sense of security against side leakage. Additionally, the design of the pattern P gives a user a good impression for its attractive appearance.

The pattern P will block liquid spreading in the side sheets 5 to further prevent leakage. Particularly because the pattern P extends substantially continuously over the whole length of the side portions 4A of the absorbent core 4, it provides a high protection against side leakage.

Since the pattern P is printed in such a configuration that the printed pattern (ink K) is substantially kept away from direct contact with the skin of a wearer, the printed ink gives no burden to the skin.

Since the pattern P is imparted by printing with ink, the original softness of the material per se of the side sheet 5 is less damaged than when the material is patterned by heat sealing as conventionally practiced. Therefore, the patterned side sheets feel agreeable.

The expression "a printed pattern (or printed ink) is substantially kept away from direct contact with the skin of a wearer" as used with reference to the first aspect of the present invention includes not only the configuration of the second embodiment in which a member exists between the ink and the skin contact surface of an absorbent article but also the configuration of the first embodiment in which the printed ink does not come into contact with the wearer's skin in ordinary use of the absorbent article (i.e., unless the printed part is strongly pressed to the skin).

The absorbent article according to the first aspect of the present invention is not limited to the foregoing embodiments, and various changes and modifications can be made without departing from the spirit and scope of the first aspect of the invention.

The absorbent article of the first aspect of the invention includes not only a sanitary napkin as described but a panty liner, an incontinence pad, etc. The first aspect of the invention is particularly suited to be applied to absorbent articles with a thickness of 2 mm or larger, a length of 150 mm or larger, or a width of 50 mm or larger.

Figure 8A:
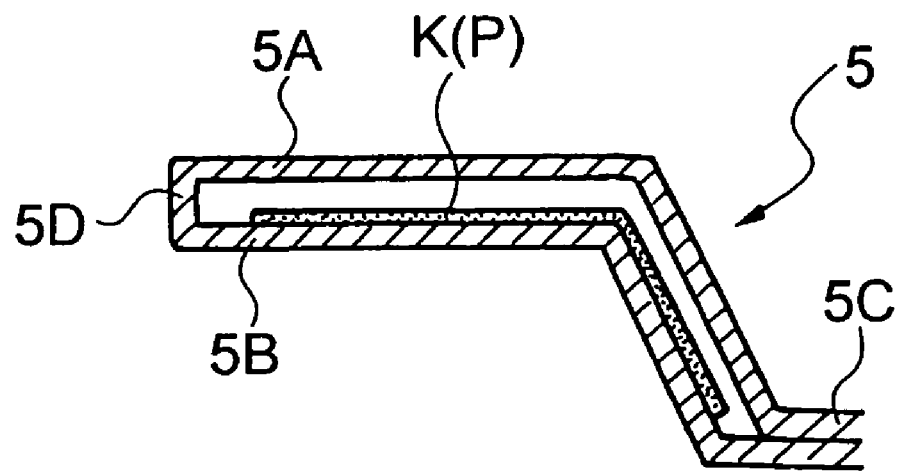
FIG. 8(a) and FIG. 8(b) each show a location of the printed pattern (ink) in the sanitary napkin according to the second embodiment.

In the embodiment where a pattern is printed on the side of the leak preventive side members that does not come into direct contact with the wearer's skin and is seen from the skin facing side through the leak preventive side members, the printing configuration is not limited to that illustrated in FIGS. 7(a), and 7(b). For example, as illustrated in FIG. 8(a), ink K may be applied to the wearer facing side of the lower panel 5B of each side sheet 5 over a region from right above the side portion of the absorbent core (not shown) to near the lower surface of the absorbent core, or, as illustrated in FIG. 8(b), ink K may be applied to the wearer facing side of the lower panel 5B of each side sheet 5 only in a region right above the side portion of the absorbent core (not shown).

Figure 9A:
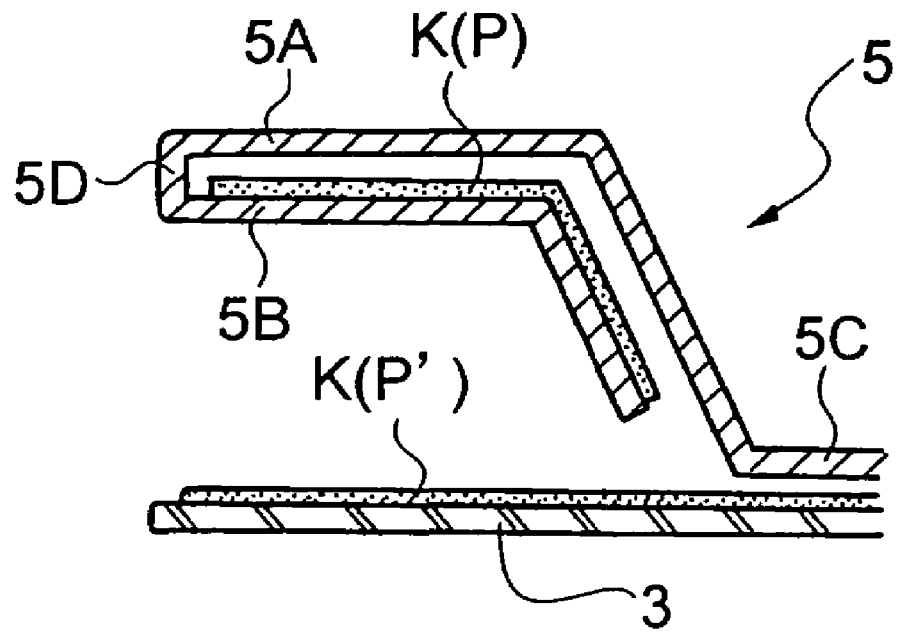
FIG. 9(a) and FIG. 9(b) each show a location of the printed pattern in the sanitary napkin according to the second embodiment.
Figure 9B:
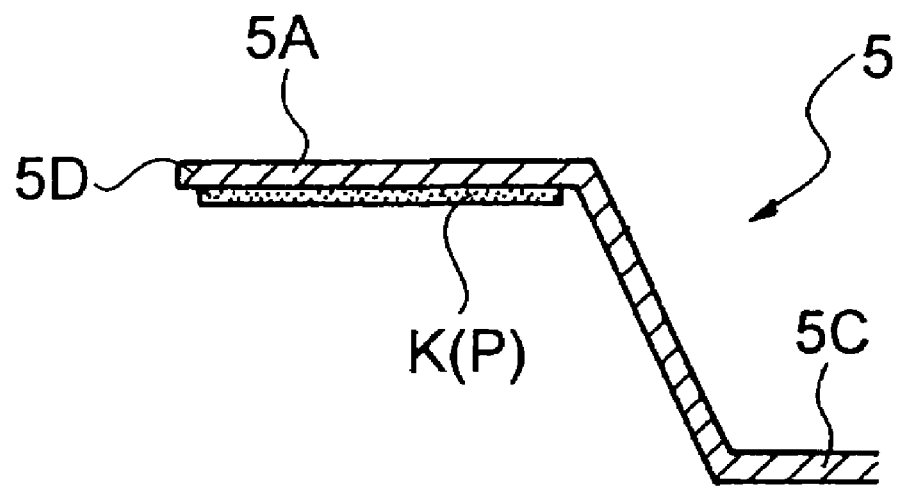

The printing configurations shown in FIGS. 9(a) and 9(b) are also included. In FIG. 9(a), unlike the configuration of FIG. 8(a), the lower panel 5B of each side sheet 5 is not in contact with the backsheet 3, and a pattern P' different from the pattern P on the side sheet 5 is formed on the skin facing side of the backsheet 3 in a region laterally outside of the absorbent core 4 in the plan view. The skin facing side of that region of the backsheet 3 is covered with the side sheet 5, and the pattern P' is seen through from the skin facing side of the side sheet 5.

Figure 8B:
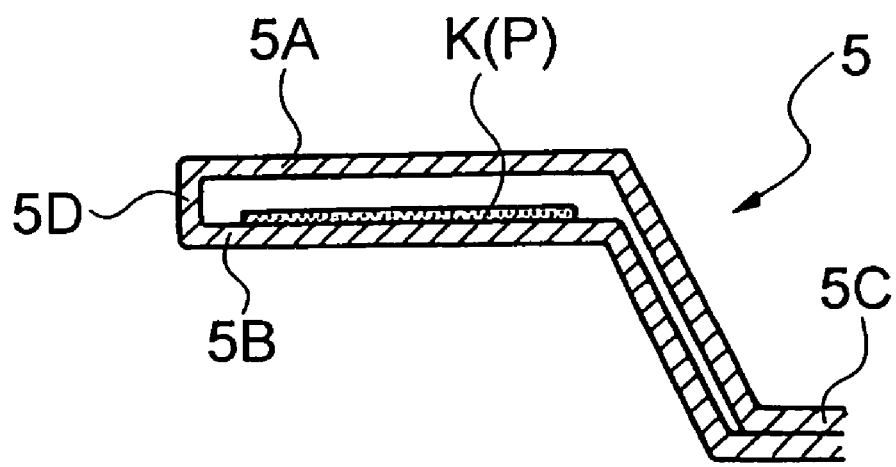

In FIG. 9(b), unlike the configuration of FIG. 8(b), the lower panel 5B of the side sheet 5 is not folded back, and the pattern P is printed on its side facing the absorbent core 4.

Figure 10:
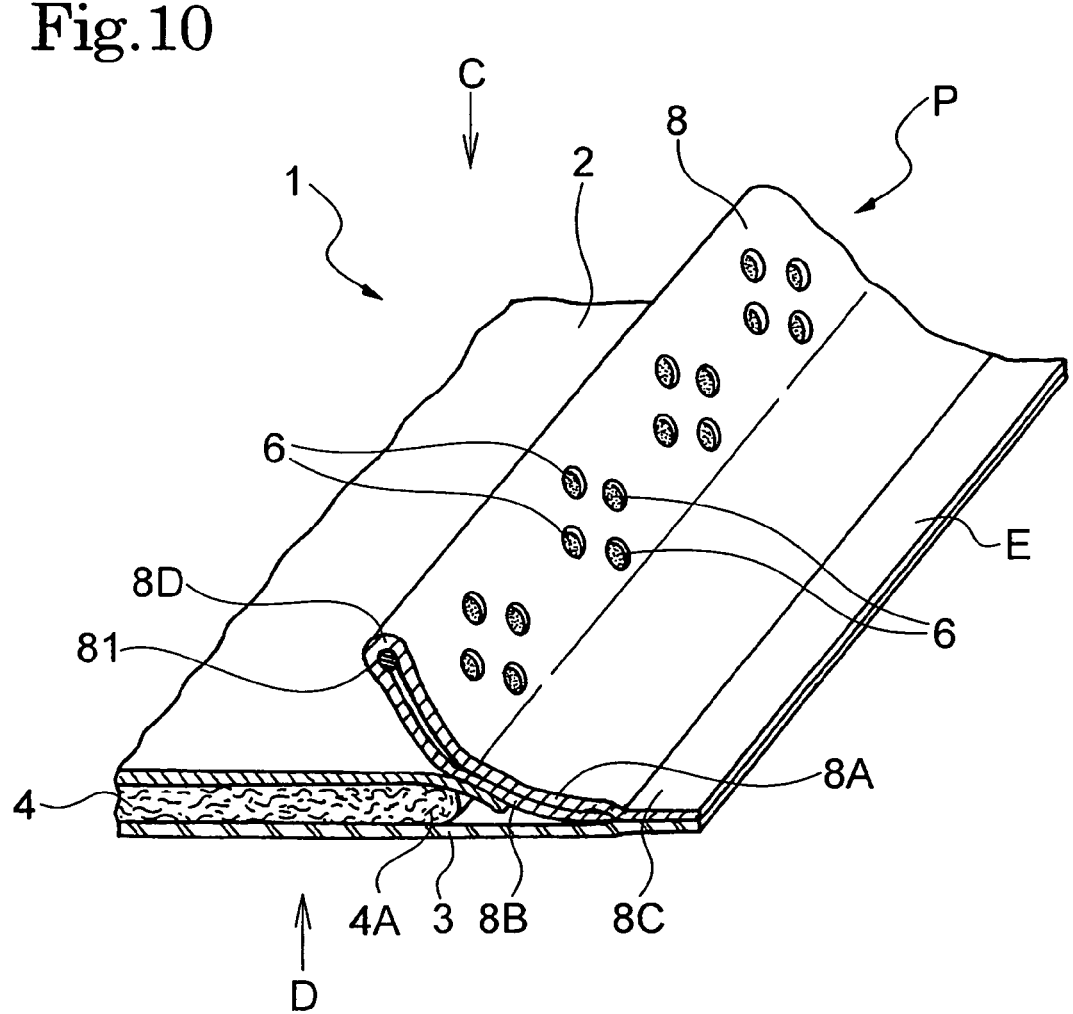
FIG. 10 is a fragmentary perspective of a cross-section of a standing cuff as a leak preventive side member (corresponding to FIG. 2(a)).

The leak preventive side members used in the first aspect of the present invention are not limited to the side sheets used in the first and the second embodiments as long as they are provided on the skin facing side of the absorbent body. For example, the leak preventive side members may be standing side cuffs 8 having a gather and standing upright on the topsheet 2 along the longitudinal side portions 4A of the absorbent core 4 as shown in FIG. 10. Each standing side cuff 8 is formed of a single sheet folded back to make an upper panel 8A and a lower panel 8B, similarly to the side sheet 5 of FIG. 2(a), with its laterally outer region 8C bonded to the laterally outer region of the backsheet 3, and with an elastic member 81 disposed longitudinally inside the inner folded edge 8D to make a standing gather.

The description about the side sheets 5 in the first and the second embodiments apply, as appropriate, to the standing side cuffs 8.

The member on which a pattern is printed is not limited only to the leak preventive side members. A pattern can be formed on leak-preventive front and rear members (not shown) provided to as overlying the skin facing side of the front and the rear end portions of the absorbent core in the plan view. A pattern can be formed on both the leak preventive side members and the leak preventive front and rear members.

The member on which a pattern is printed is not limited to those separate from the topsheet, such as the side sheets 5 and the standing cuffs 8. A pattern can be formed on the skin facing side (outside) or the side facing an absorbent core (inside) of the topsheet in a region overlying with the side portions or the front and the rear end portions of the absorbent core in the plan view.

When a pattern is formed on the leak preventive front and rear members or the topsheet, the description about the side sheets 5 or the standing cuffs 8 also applies as appropriate.

A pattern can be formed in not only a region right above the side portions of the absorbent core but in a region laterally extending outward from that region.

The shape of the depression in the plan view includes a circle as of the depressions 6 in the first embodiment and any other shapes such as a straight line, a curved line and other patterns.

The shape of the pattern units formed on a surface that does not come into direct contact with a wearer is not limited to the closed loops and wavy lines as of the pattern in the second embodiment and includes a circle, a straight line, other curved lines and other patterns.

The elements and configurations described above primarily with reference to the first and the second embodiments may be combined appropriately. For instance, a pattern formed by transferring ink to the bottom of depressions may be a pattern formed on a pair of leak preventive side members in a region extending laterally outward from right above the side portions of the absorbent core and composed of pattern units arranged to extend substantially continuously over a length of 50% or more of the whole length of the side portions of the absorbent core in the plan view. A pattern printed on the side of a pair of leak preventive side members that does not come into direct contact with the skin of a wearer and seen through from the skin facing side of the side members may be a pattern made up of circular pattern units in the plan view.

Figure 11A:
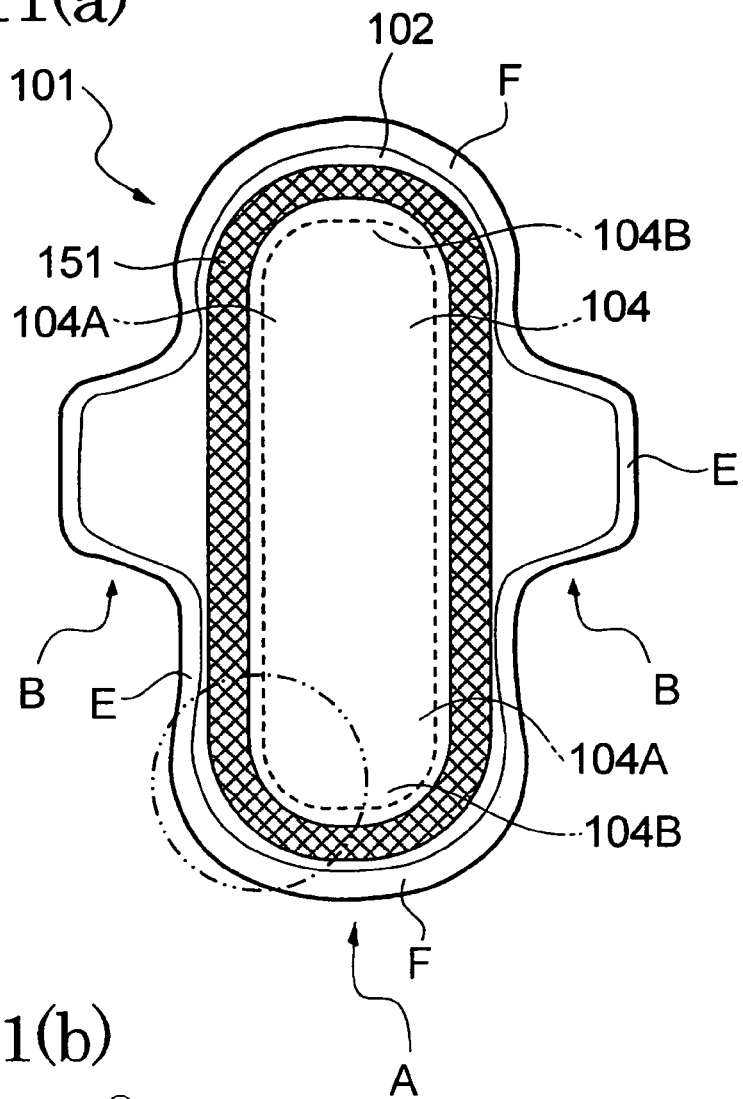
FIG. 11(a) is a plan view of a sanitary napkin according to an embodiment of the absorbent article according to the second aspect of the invention (a third embodiment).
Figure 11B:
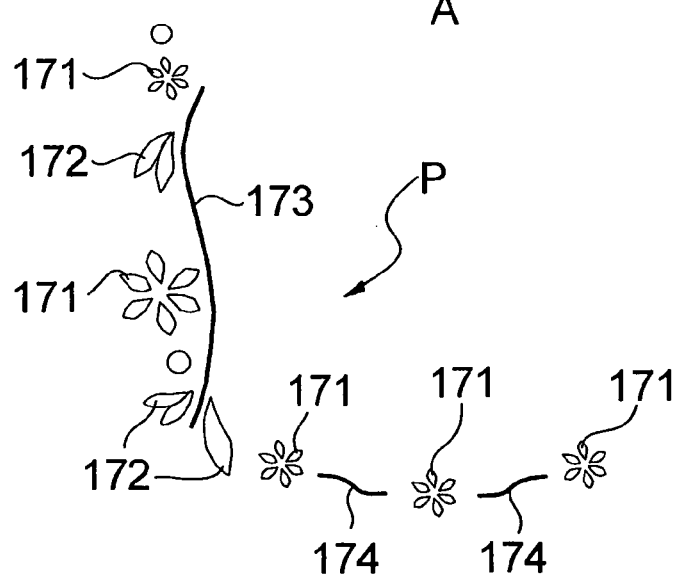
FIG. 11(b) is an enlarged view of the pattern in the double dashed chain line circle in FIG. 11(a).
Figure 14A:
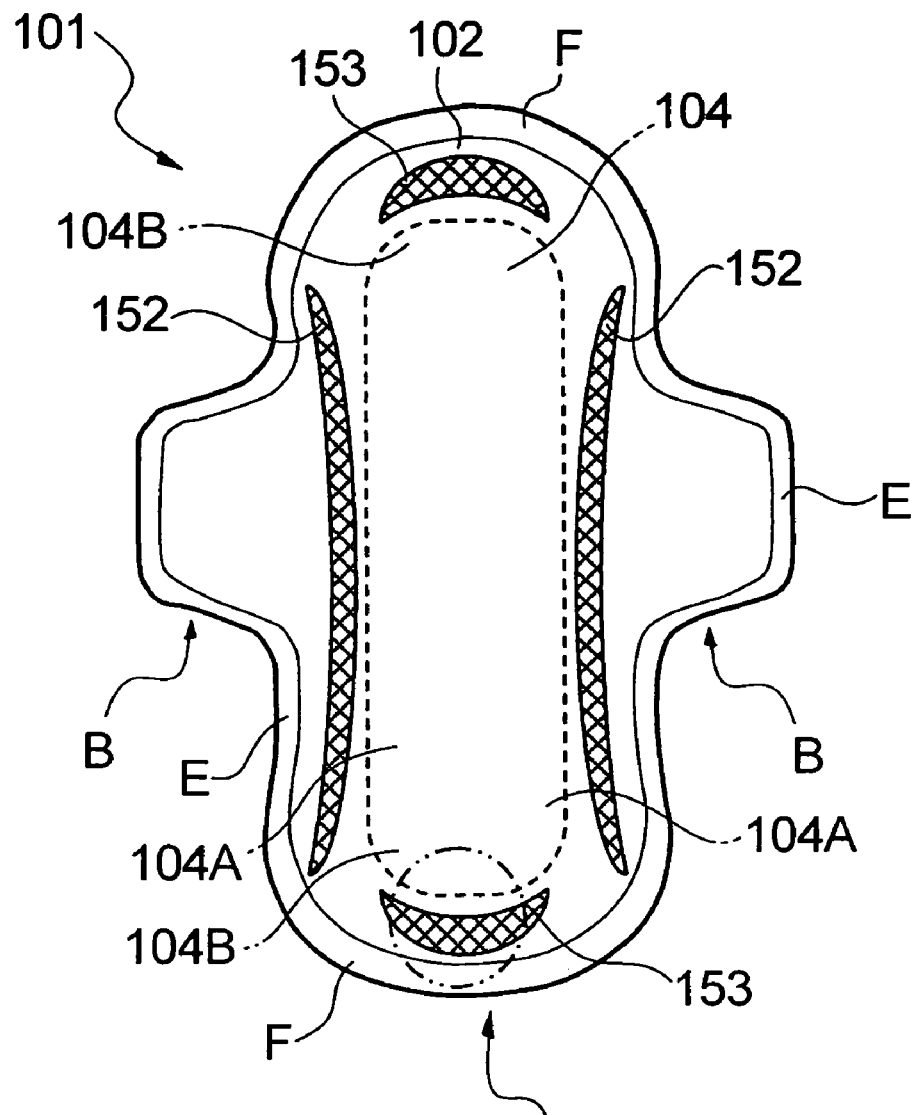
FIG. 14(a) is a plan view of a sanitary napkin according to another embodiment of the absorbent article according to the second aspect of the present invention (a fourth embodiment).

The absorbent article according to the second aspect of the present invention will then be described with reference to its preferred embodiment, a third embodiment of the present invention, by way of FIGS. 11(a), 11(b), 12(a), and 12(b). In FIG. 11(a), the cross-hatched region indicates a region where a pattern is formed. This does not mean that the pattern is printed solid over the entire area of that region. The cross-hatched region indicates the broad outline of a pattern. The same applies to FIG. 14(a), et seq. FIG. 11(b) presents an enlarged view of the pattern in the double dashed line circle in FIG. 11(a).

As illustrated in FIGS. 11(a), 11(b), 12(a), and 12(b), the sanitary napkin 101 of the third embodiment has a substantially oblong rectangular absorbent body A and a pair of wings B laterally extending from both longitudinal side edges of the absorbent body A. The absorbent body A is composed of a liquid permeable topsheet 102, a liquid impermeable backsheet 103, and a liquid retentive absorbent core 104 interposed between the two sheets. The absorbent body A has a skin facing side C and a garment facing side D.

The skin facing side C of the absorbent body A has partly depressed in its thickness direction to form depressions 106 in a region outside of the absorbent core 104 and has ink K transferred to the bottom 161 of the depressions 106 to form a printed pattern P. More specifically, the topsheet 102 has depressions 106 and the printed pattern P on its skin facing side. The term "region outside of the absorbent core" is intended to indicate a region except the overlap with the absorbent core in the plan view, including laterally outer regions along both the longitudinally extending side edges of the absorbent core and longitudinally outer regions along the front and the rear ends of the absorbent core.

In the absorbent body A, the topsheet 102 covers the entire upper side of the absorbent core 104 and extends laterally outward from the longitudinally extending side portions 104A of the absorbent core 104 and longitudinally from the front and the rear ends 104B of the absorbent core 104 and overlies the outer region of the backsheet 103.

The topsheet 102 can be made of various materials, such as nonwoven fabric, a perforated film, and a composite thereof. In case when the topsheet 102 is to be embossed to form the depressions 106 in which ink is transferred to form the pattern P as hereinafter described, the topsheet material should be selected from those capable of being embossed and printed. In the third embodiment, hydrophilic nonwoven fabric is used as the topsheet 102.

The backsheet 103 covers the entire lower side of the absorbent core 104 and extends laterally outward from the side portions 104A of the absorbent core 104 and longitudinally from the front and the rear ends 104B of the absorbent core 104.

The backsheet 103 may have breathability. The backsheet 103 does not need to have perfect liquid impermeability so that a hardly liquid permeable sheet will do. The backsheet 103 is not particularly limited. In this particular embodiment, a leakproof plastic film is used. A film with micropores, nonwoven fabric, or a composite thereof is also useful. Where a leakproof sheet is interposed between the absorbent core and the backsheet, the backsheet, which defines the garment facing side D, does not need to have liquid impermeability.

The absorbent core 104 can be of any material known in the art.

As shown in FIG. 11(a), a pair of wings B are provided on both sides of the target zone of the absorbent body A. The wings B are formed of the laterally outer regions of the backsheet 3 and the laterally outer regions of the topsheet 102.

Figure 12A:
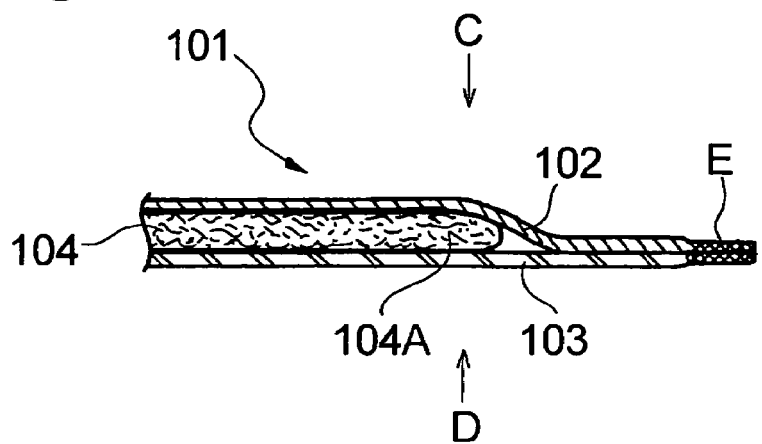
FIG. 12(a) is a transverse cross-sectional view of the sanitary napkin according to the third embodiment.

The backsheet 103 and the topsheet 102 are bonded together in their peripheral region along the side edges of the absorbent body A and along the periphery of the wings B to form side seals E as shown in FIGS. 11(a) and 12(a). The topsheet 102 and the backsheet 103 are also bonded together along the front and the rear edges of the absorbent body A to form end seals F as shown in FIG. 11(a). As illustrated in FIG. 12(a), the backsheet 103 and the topsheet 102 are also bonded together in a region near the side portions 104A of the absorbent core 104 and in the wings B with an adhesive (not shown).

The sanitary napkin 101 of the third embodiment is worn by attaching the napkin 101 to an undergarment via a hot-melt pressure-sensitive adhesive (not shown) applied to the garment facing side D of the absorbent body A and the wings B and folding the wings B over the sides of the undergarment in the crotch region to secure the napkin 101.

Figure 12B:
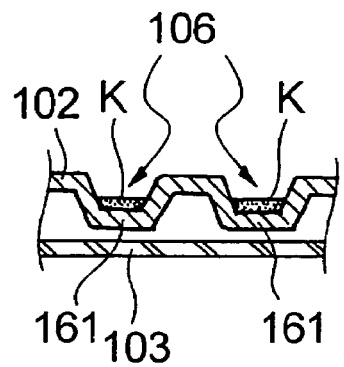
FIG. 12(b) is a cross-sectional view taken across depressions.

As illustrated in FIG. 12(b), the topsheet 102 has depressions 106 in its thickness direction and has ink K transferred to the bottom 161 of the depressions 106 to form a printed pattern P shown in FIG. 11(b). The depressions 106 are formed by patternwise embossing the topsheet 102. The individual depressions 106 preferably have a diameter or a width of 0.5 to 5.0 mm.

The ink that can be used in the present invention includes inorganic pigments and organic pigments. Organic pigments, particularly those having relatively high heat stability are preferred from the standpoint of ease of handling and smooth prosecution of steps involved, particularly in view of stability with time and the fact that the depressions 106 are preferably formed by heat embossing. Use of an adhesive, particularly a hot-melt adhesive, having the pigment incorporated therein as ink is advantageous in that the depressions 106 are formed more easily and that bonding to other members is achieved more easily. Where ink is transferred to the bottom 161 of the depressions 106 of the topsheet 102, etc. to form the pattern P as described infra, printing techniques useful to achieve such a printing method include relief printing and gravure printing.

As illustrated in FIG. 11(*b*), the pattern P is made of a combination of pattern units, such as a petal pattern unit 171, a leaf pattern unit 172, a long, elongated s-shape pattern unit 173, and a short, elongated s-shape pattern unit 174, arranged in the peripherally outer region of the absorbent core 104. The pattern P is formed in a pattern region 151 surrounding the perimeter of the absorbent core 104 in FIG. 11(*a*). The pattern P is arranged in the pattern region 151 so as to substantially surround the perimeter of the absorbent core 104.

The expression "substantially surrounding the perimeter of the absorbent core" is defined to have the following meaning. Move an imaginary half line extending outward from, and normal to, the perimeter of an absorbent core along the perimeter of the absorbent core in the plan view of the absorbent article. When the half line intersects the pattern P (a combination of the petal pattern units 171, the leaf pattern units 172, the long, elongated S-shaped curves 173, and the short, elongated S-shaped curves 174, etc. in the third embodiment) over a length of 80% or more of the whole circumference of the absorbent core, the pattern is said to "substantially surround the perimeter of the absorbent core".

The topsheet 102 having the pattern P formed by transferring ink K to the bottom 161 of the depressions 106 is obtained by various methods. The method depicted in FIG. 13 is one of them.

Figure 13:
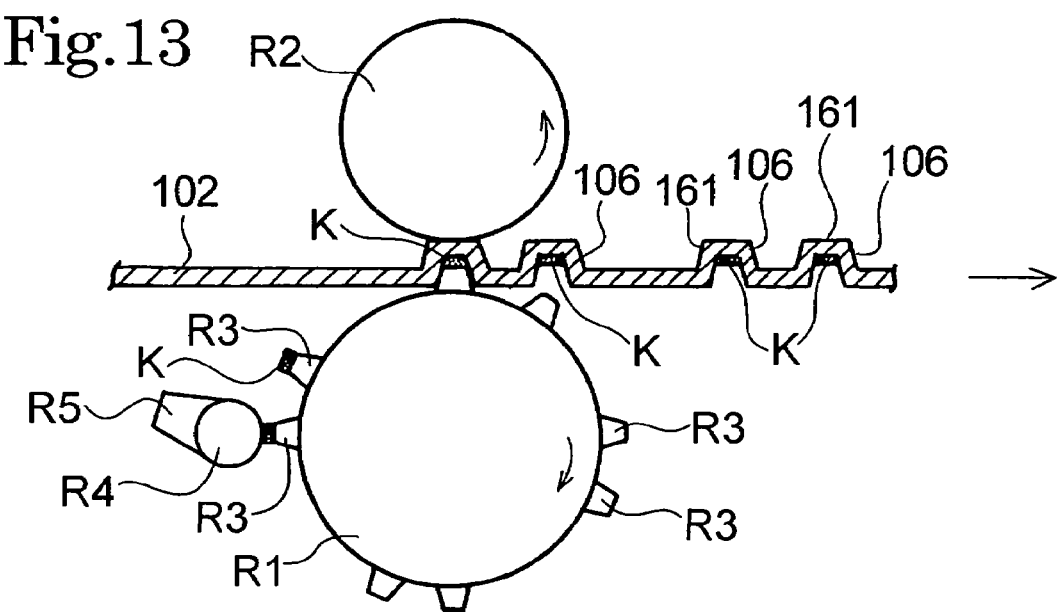
FIG. 13 schematically illustrates a method of printing a pattern on the topsheet in the third embodiment.

The method of FIG. 13 is effected using an embossing roll R1 and a backup roll R2. The embossing roll R1 has projections R3 corresponding to the depressions 106 of the topsheet on its peripheral surface, and the backup roll R2 has a smooth peripheral surface. In the method shown in FIG. 13, the embossing roll R1 and the backup roll R2 are located below and above a web of the topsheet 102, respectively, and an ink trough R5 containing ink K and an ink roller R4 are placed beside the embossing roll R1.

As the embossing roll R1 rotates, the ink K in the ink trough R5 adheres via the ink roller R4 to the top of the projections R3 of the embossing roll R1 as in relief printing beside the embossing roll R1. At the upper part of the embossing roll R1, the web of the topsheet 102 is embossed between the backup roll R2 and the projections R3 with the ink K adhered thereto. As a result, the web of the topsheet 102 has upward depressions 106 with the ink K adhered to their bottom 161.

Since the sanitary napkin 101 of the third embodiment has the pattern P printed on the topsheet 102, it has an improved preventive effect against leakage. The pattern P makes a user realize the improvement and feel secured. To explain in more detail, the absorbent body A has depressions 106 on its skin facing side C in a region outside of the absorbent core 104 in the plan view with ink K transferred to the bottom 161 of the depressions 106 to form the pattern P. Therefore, liquid spreading in the topsheet 102 will be blocked by the pattern P. Arranged to substantially surround the perimeter of the absorbent core 104, the pattern P exhibits high effect in preventing leakage. The pattern P easily catches the user's eye and makes the user realize its improved effect on leakage prevention. This gives a wearer a sense of security against leakage. Additionally, the design of the pattern P lends an attractive appearance to the absorbent article, giving a good impression to the wearer.

Moreover, liquid spreading on the surface (the skin facing side) of the topsheet 102 will flow into the depressions 106, which further improves prevention against leakage. When in using hydrophobic or water-repellent ink as ink K, the ink transferred to the bottom of the depressions fills the interstices between fibers, etc. of the topsheet to produce an enhanced effect in suppressing liquid from spreading, which provides particularly high protection against leakage.

Since the pattern P is formed by ink K transferred to the bottom 161 of the depressions 106, it is substantially kept away from direct contact with the skin of a wearer. Therefore, the printed ink causes no burden to the skin, giving no discomfort to the skin nor impairing the softness of the topsheet. The expression "substantially kept away from direct contact with the skin of a wearer" as used in the second aspect of the present invention means that the printed ink does not come into contact with the wearer's skin in ordinary use of the absorbent article.

Since the pattern P is imparted by printing with ink, the original softness of the material per se of the topsheet 102 is less damaged than when the material is patterned by heat sealing as conventionally practiced. Therefore, the patterned region feel agreeable.

Figure 14B:
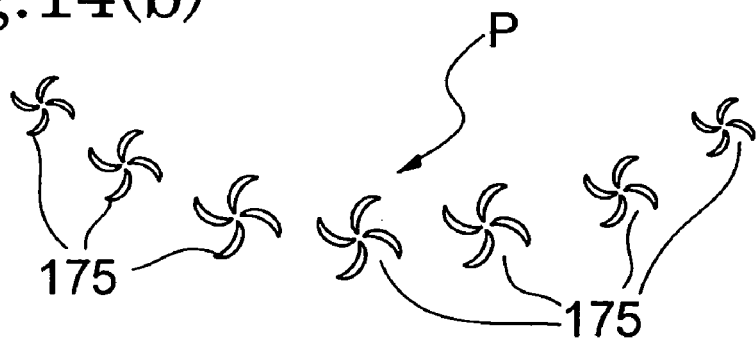
FIG. 14(b) is an enlarged view of the pattern in the double dashed chain line circle in FIG. 14(a).

Another embodiment of the second aspect of the present invention, a fourth embodiment of the present invention, will be described by way of FIGS. 14(*a*) and 14(*b*). FIG. 14(*b*) is an enlarged view of the pattern in the double dashed chain line circle in FIG. 14(*a*).

The fourth embodiment is different from the third one in the design and the location of the pattern. The fourth embodiment will be described primarily with reference the difference from the third one. Elements identified with the same numerals as in the third embodiment may be identical and will not be redundantly described. The description relating to the third embodiment applies to the fourth one as appropriate.

The sanitary napkin 101 of the fourth embodiment has an absorbent body A and a pair of wings B similarly to the third embodiment as shown in FIG. 14(*a*). A pattern P is formed in a pattern region 152 along each side portion 104A of the absorbent core 104 substantially continuously in the longitudinal direction of the absorbent core 104. A pattern P is also formed in a pattern region 153 along each of the front and the rear ends 104B of the absorbent core 104 substantially continuously in the lateral direction of the absorbent core 104.

As illustrated in FIG. 14(*b*), the pattern P in the pattern regions 152 along each side portion 104A of the absorbent core 104 and the pattern regions 153 along each of the front and the rear ends 104B of the absorbent core 104 is made up of pattern units 175 aligned to depict an arc. Each pattern unit 175 is composed of four crescent-shaped subunits arranged at right angles into a pinwheel shape.

The expression "substantially continuous(ly) in the longitudinal direction" as used herein is defined as follows. Move an imaginary straight line perpendicular to the longitudinal direction (i.e., a laterally extending straight line) in the longitudinal direction in the plan view of the absorbent article. When the line intersects the pattern P (a repetition of the pattern units 175) over a length of 80% or more of the whole length of the absorbent core, the pattern is said to be "substantially continuous in the longitudinal direction". Likewise, the expression "substantially continuous(ly) in the lateral direction" is defined as follows. Move an imaginary straight line perpendicular to the lateral direction (i.e., a longitudinally extending straight line) in the lateral direction in the plan view of the absorbent article. When the line intersects the pattern P over a distance of 80% or more of the whole width of the absorbent core, the pattern is said to be "substantially continuous in the lateral direction".

The sanitary napkin 101 of the fourth embodiment produces the same effects as with the one of the third embodiment and has an attractive appearance appealing to a user owing to its pattern.

The absorbent article according to the second aspect of the present invention is not limited to the foregoing embodiments, and various changes and modifications can be made without departing from the spirit and scope of the second aspect of the invention.

The absorbent article of the second aspect of the invention includes not only a sanitary napkin as described but a panty liner, an incontinence pad, etc. The second aspect of the invention is particularly suited to be applied to absorbent articles with a thickness of 2 mm or larger, a length of 150 mm or larger, or a width of 50 mm or larger.

Figure 15:
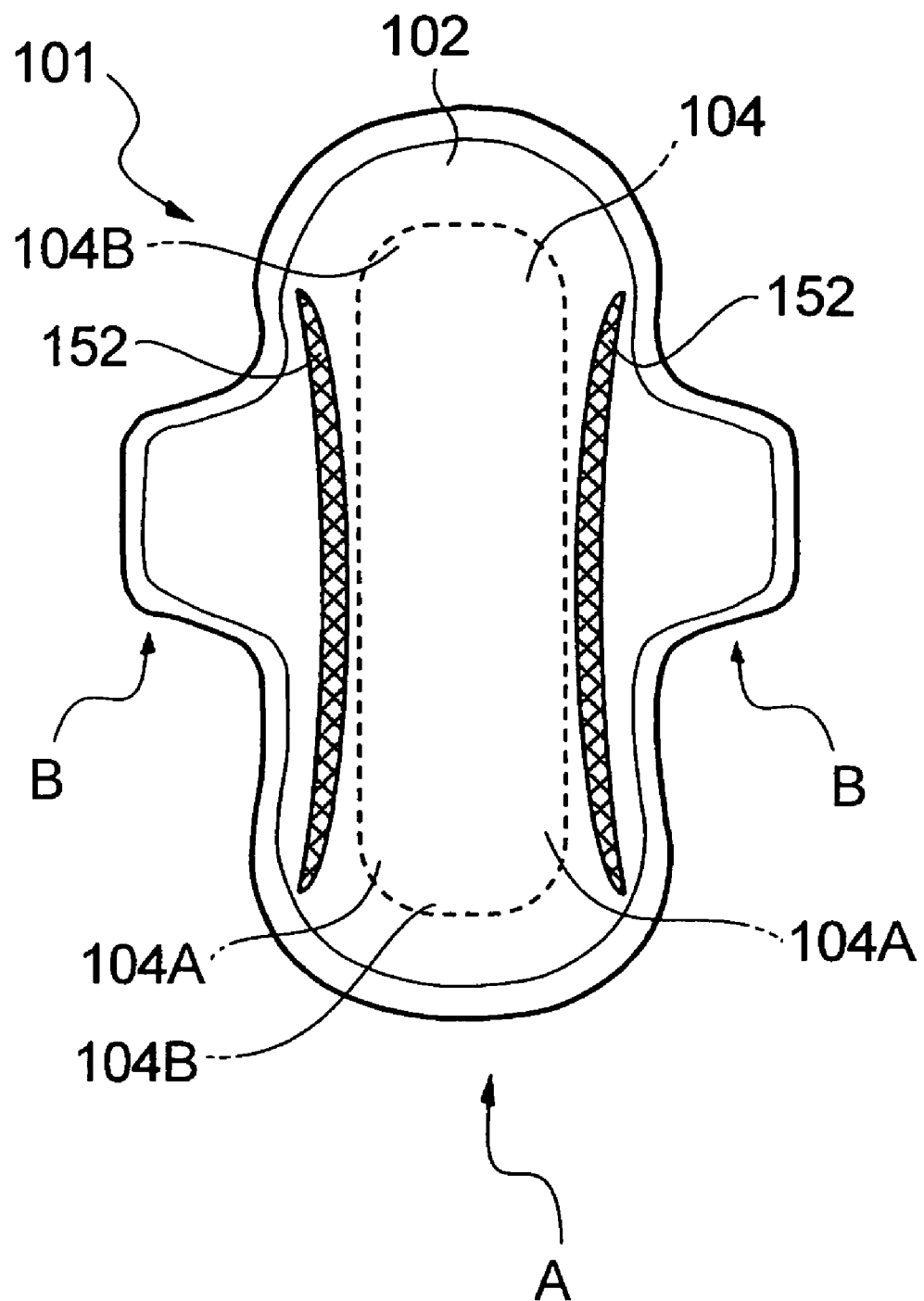
FIG. 15 is a plan view of a sanitary napkin according to still another embodiment of the second aspect of the present invention.
Figure 16:
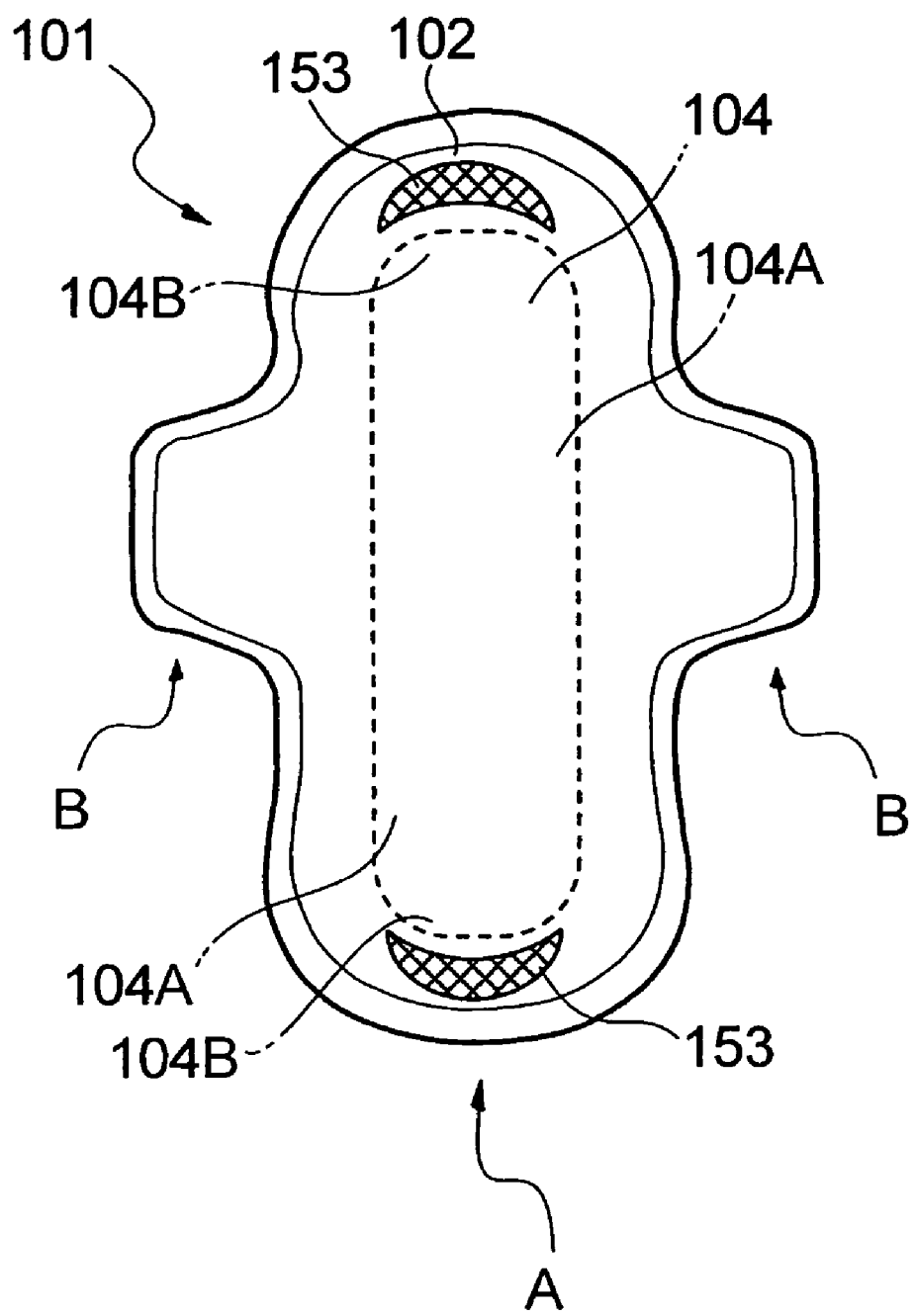
FIG. 16 is a plan view of a sanitary napkin according to still another embodiment of the second aspect of the present invention.

The location of pattern formation is not limited to those adopted in the third and the fourth embodiments as long as it is outside of the absorbent core in the plan view. For instance, a pattern P may be formed only in the pattern regions 152 along the side portions 104A but not along the front and the rear ends 104B of the absorbent core 104 as in FIG. 15. In this case, improvement on prevention of side leakage is obtained. To the contrary, a pattern P may be formed only in the pattern regions 153 along each of the front and the rear ends 104B of the absorbent core 104 but not along each side portion 104A of the absorbent core 104 as in FIG. 16. In this case, improvement on prevention of front and rear leakage is obtained.

Figure 17:
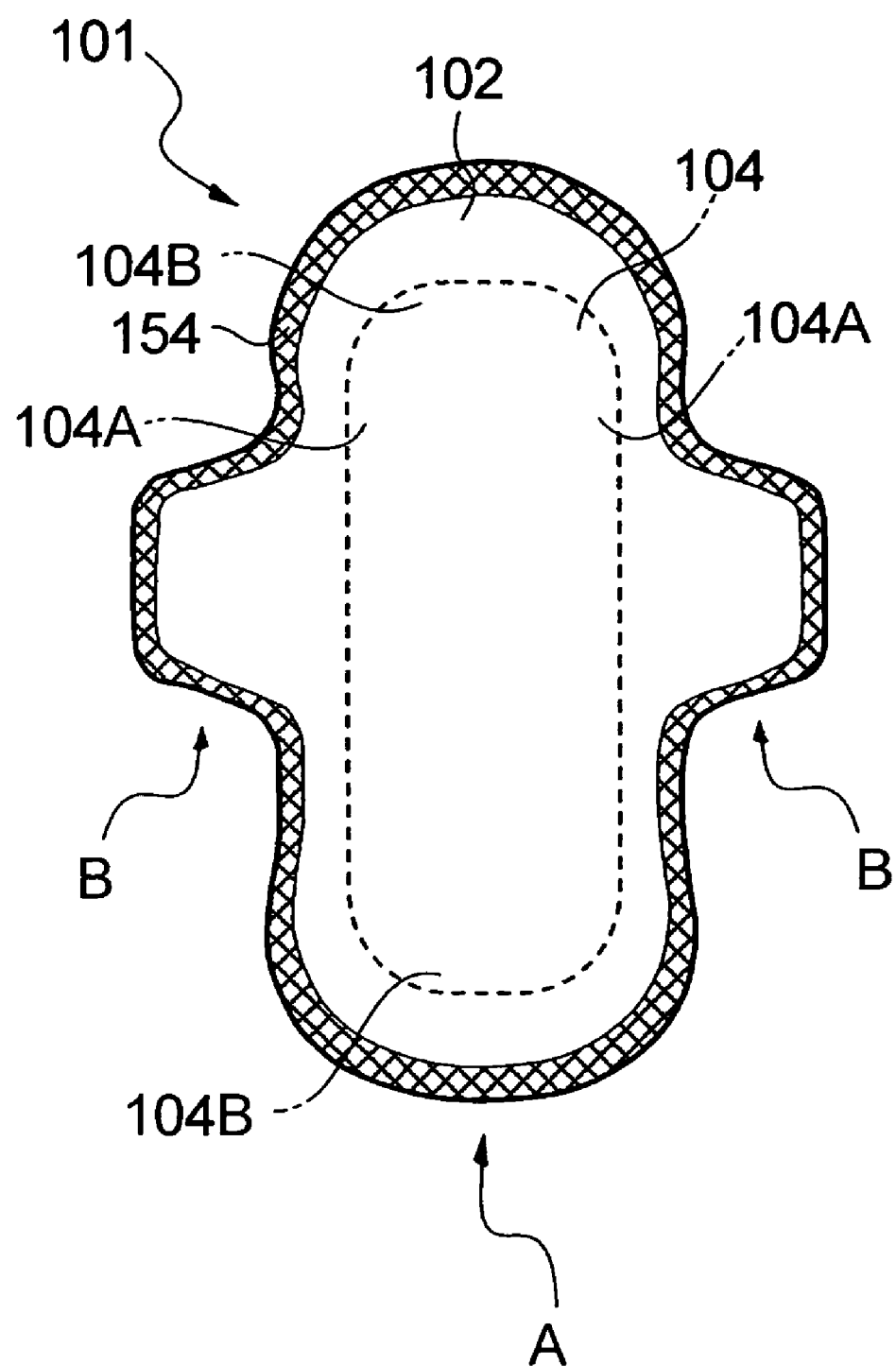
FIG. 17 is a plan view of a sanitary napkin according to still another embodiment of the second aspect of the present invention.

A pattern P may be formed along the perimeter of an absorbent article 101, inclusive of the perimeter of the wings B as shown in FIG. 17. That is, a pattern P may be formed in a pattern region 154 continuously extending along the whole perimeter of an absorbent article, and the pattern units of the pattern P are arranged in the region 154 substantially continuously along the whole perimeter of the absorbent article. In this case, improvement on prevention of leakage along the whole perimeter of the absorbent article is obtained. The expression "substantially continuous(ly) along the whole perimeter of an absorbent article" means that, when an imaginary half line extending inward from, and normal to, the perimeter of an absorbent article is moved along the perimeter of the absorbent article in the plan view, the half line intersects the pattern P over a length of 80% or more of the whole perimeter of the absorbent article.

Figure 18:
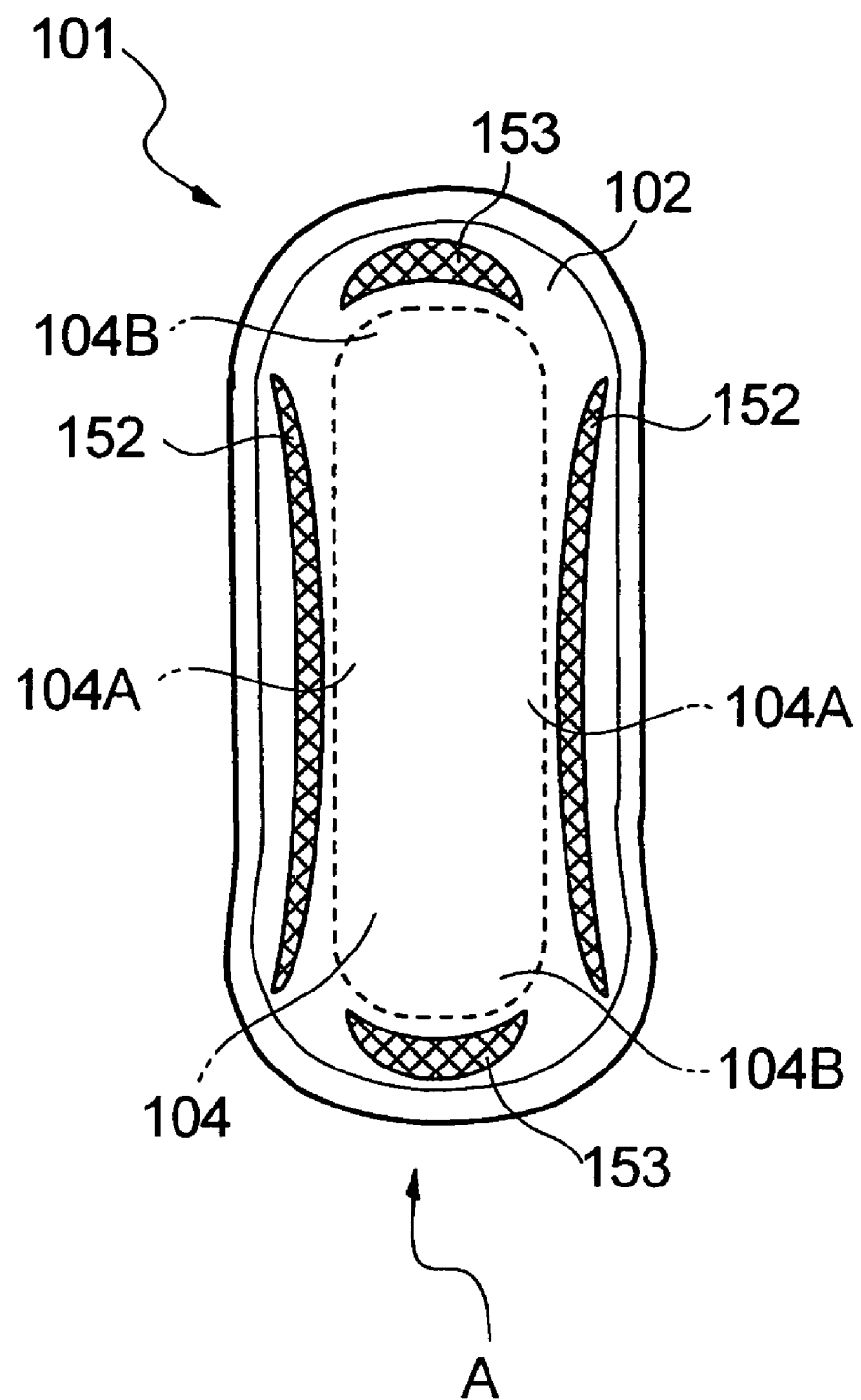
FIG. 18 is a plan view of a sanitary napkin according to still another embodiment of the second aspect of the present invention.

The second aspect of the present invention is also applicable to wingless absorbent article as shown in FIG. 18.

Figure 19A:
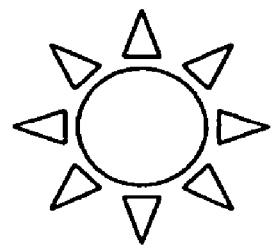
FIG. 19(a), FIG. 19(b), FIG. 19(c), FIG. 19(d), and FIG. 19(e) representatively show pattern units.
Figure 19B:
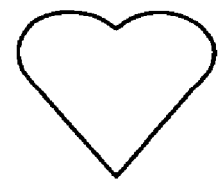
Figure 19C:
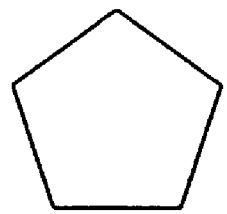
Figure 19D:
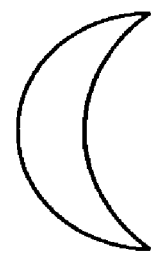
Figure 19E:

The pattern to be formed is not limited to those of the third and the fourth embodiments. FIG. 19 illustrates a few examples of other pattern units, in which FIG. 19(a) is a sun, FIG. 19(b) a heart, FIG. 19(c) a regular pentagon, FIG. 19(d) a crescent, and FIG. 19(e) anthropomorphic fruit.

Figure 20A:
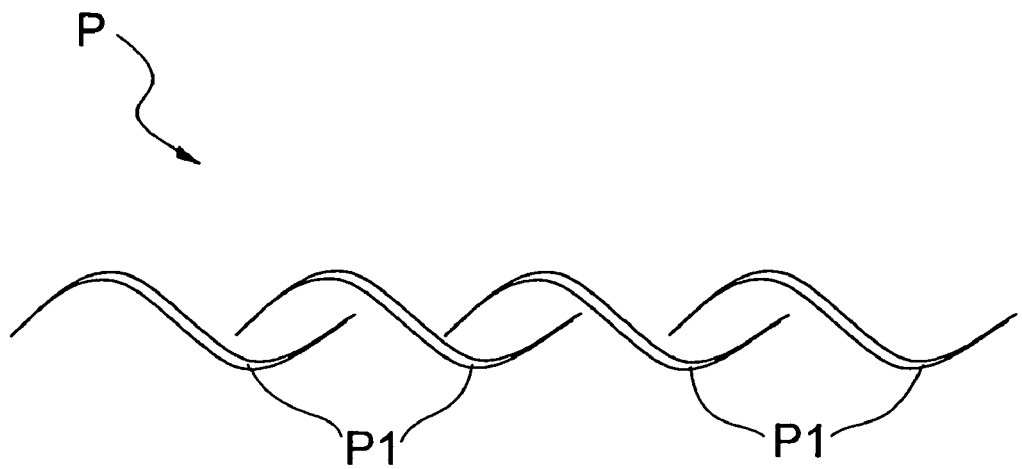
FIG. 20(a) and FIG. 20(b) each show a pattern.
Figure 20B:
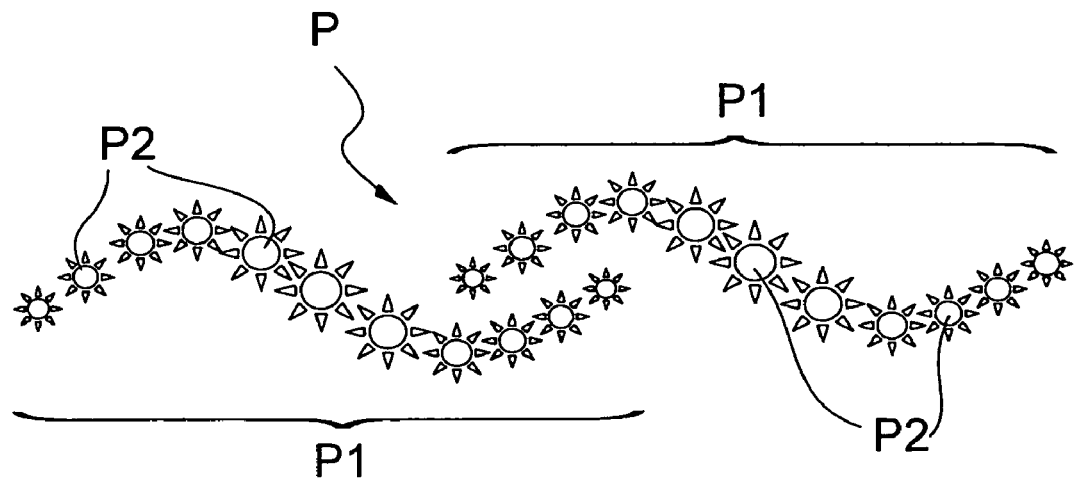

As depicted in FIG. 20(a), elongated s-shaped pattern units P1 may be aligned in a chain to form a substantially continuous pattern P. As illustrated in FIG. 20(b), a substantially continuous pattern P may be formed of a chain of elongated s-shaped pattern units P1 each composed of sun pattern subunits P2 of varying sizes.

A pattern or a pattern unit may be arranged intermittently along the side edges, the front and the rear end edges or the perimeter of the absorbent core.

The member on which a pattern is printed is not limited to the topsheet and may be formed on the skin facing side of other members separate apart from the absorbent body, such as a pair of side sheets or a pair of standing side cuffs.

The elements and configurations of the second aspect of the present invention described above primarily with reference to the third and the fourth embodiments may be combined appropriately.

Figure 21:
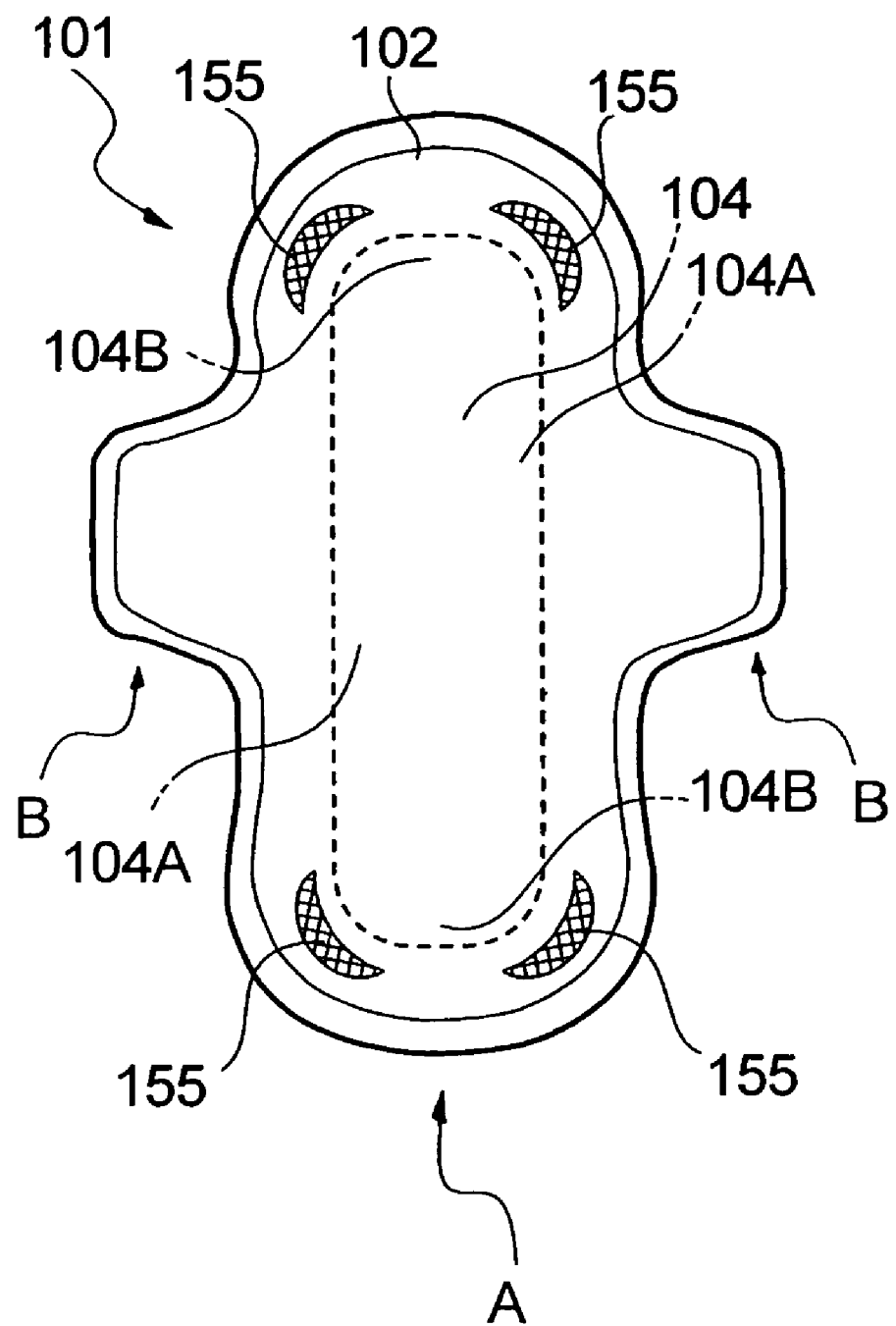
FIG. 21 is a plan view of a sanitary napkin of still another embodiment of the second aspect according to the present invention.

A pattern may be formed on either one of the pattern regions 153 along the front and the rear ends 104B of the absorbent core 104 (see FIG. 16) without being formed on the other pattern region. As shown in FIG. 21, a pattern region 155 may be disposed on four corners of an absorbent article in an area outside of the four corners of the absorbent core (where the side portions 104A and the front and the rear ends 104B of the absorbent core intersect). In this way, a pattern can be formed in an appropriate region that needs enhanced prevention against leakage.

The wings may be formed of sheets joined to both sides of the absorbent body independently of the topsheet and the backsheet.

The elements and configurations of the embodiments according to the first aspect of the present invention and those of the embodiments according to the second aspect of the present invention can be used in appropriate combination.

Effect of the Invention:

According to the first aspect of the invention, since an absorbent article has a pattern printed on leak preventive side members, it makes a user aware of the existence of the leak preventive side members and gives the user a sense of security against side leakage. The pattern, while formed by printing with ink, causes no burden on the skin. Additionally, the design of the pattern lends an attractive appearance to the absorbent article.

According to the second aspect of the invention, an absorbent article having a pattern printed exhibits improved leak-proofness and makes a user realize the improvement and therefore feel secured.

What is claimed is:

1. An absorbent article comprising a substantially oblong rectangular absorbent body having a skin facing side and comprising a topsheet, a backsheet, and an absorbent core between the topsheet and the backsheet, the absorbent article further comprising a pair of leak preventive side members on the skin facing side of the absorbent body, the leak preventive side members having a pattern printed with ink in a configuration such that the printed ink is substantially kept away from contact with the skin of a wearer, wherein the leak preventive side members each have depressions in the thickness direction thereof, which depressions open on a top surface of the skin facing side of the absorbent article and have ink in the bottom of the depressions to form the pattern.

2. The absorbent article according to claim 1, wherein the leak preventive side members each overlies each longitudinally extending side portion of the absorbent core.

3. The absorbent article according to claim 1, wherein the pattern is printed on the side of the leak preventive side members that does not come into direct contact with the skin of a wearer and is seen through the leak preventive side members from the skin facing side.

4. The absorbent article according to claim 1, wherein the leak preventing side members each have the pattern printed in a region of from right above a longitudinally extending side portion of the absorbent core and extending laterally outward from the absorbent core.

5. The absorbent article according to claim 1, wherein a pattern different from the pattern of the leak preventive side members is formed on the skin facing side of the backsheet in outer regions laterally outside of the absorbent core, the skin facing side of the outer regions of the backsheet being covered with the respective leak preventive side members, and the pattern of the outer regions of the backsheet being seen through from the skin facing side of the leak preventive side members.

6. The absorbent article according to claim 1, wherein the leak preventive side members are each a side sheet provided on the skin facing side of the absorbent body, the side sheet covering a longitudinally extending side portion of the absorbent core and extending from the absorbent core laterally outward to cover the topsheet and the backsheet.

7. The absorbent article according to claim 1, wherein said depressions have ink on the entire surface of the bottom of the depressions to form the pattern.

8. An absorbent article comprising a substantially oblong rectangular absorbent body having a skin facing side and comprising a topsheet, a backsheet, and an absorbent core between the topsheet and the backsheet, the absorbent body having depressions in the thickness direction on the skin facing side in a region outside of the absorbent core, which depressions open on a top surface of the skin facing side of the absorbent body, and having ink in the bottom of the depressions to have a pattern printed.

9. The absorbent article according to claim 8, wherein the pattern is formed along the perimeter of the absorbent core, and the pattern formed along the periphery of the absorbent core is arranged to substantially surround the perimeter of the absorbent core.

10. The absorbent article according to claim 8, wherein the pattern is formed along each longitudinally extending side portion of the absorbent core, and the pattern formed along each side portion of the absorbent core is arranged substantially continuously in the longitudinal direction of the absorbent body.

11. The absorbent article according to claim 8, wherein the pattern is formed along at least one of the front end and the rear end of the absorbent body, and the pattern formed along the front and/or the rear end of the absorbent body is arranged substantially continuously in the width direction of the absorbent body.

12. The absorbent article according to claim 8, further comprising a pair of wings extending laterally outward from both longitudinal sides of the absorbent body, wherein the pattern is formed along the perimeter of the absorbent article inclusive of the perimeter of the wings, and the pattern formed along the perimeter of the absorbent article is arranged substantially continuously along The whole perimeter of The absorbent article.

13. The absorbent article according to claim 8, wherein said depressions have ink on the entire surface of the bottom of the depressions to form the pattern.

* * * * *